United States Patent [19]

Isberg et al.

[11] Patent Number: 5,338,842
[45] Date of Patent: Aug. 16, 1994

[54] YERSINIA INV NUCLEIC ACIDS

[75] Inventors: Ralph R. Isberg, Brookine, Mass.; Virginia Miller, Los Angeles; Stanley Falkow, Portola Valley, both of Calif.

[73] Assignee: The Board of Trustees of Leland Stanford Jr. University, Stanford, Calif.

[21] Appl. No.: 890,317

[22] Filed: May 22, 1992

Related U.S. Application Data

[63] Continuation of Ser. No. 559,904, Jul. 30, 1990, abandoned, which is a continuation-in-part of Ser. No. 340,375, Apr. 19, 1989, which is a continuation-in-part of Ser. No. 761,222, Jul. 31, 1985, abandoned.

[30] Foreign Application Priority Data

Apr. 18, 1990 [WO] PCT Int'l Appl. ............... PCT/US90/02131

[51] Int. Cl.$^5$ .................. C12N 15/31; C12N 1/21; C12Q 1/68
[52] U.S. Cl. ........................... 536/23.7; 435/6; 435/69.1; 435/252.3; 435/252.33; 435/320.1; 536/24.32
[58] Field of Search .............. 536/27, 23.7, 24.32; 435/172.3, 320.1, 252.3, 252.33, 6, 69.1; 935/11, 72, 173

[56] References Cited

FOREIGN PATENT DOCUMENTS 0211543 2/1987 European Pat. Off. ...... C12N 15/00
90/12867 11/1990 World Int. Prop. O. ...... C12N 1/21

OTHER PUBLICATIONS

Small, P. L. C. et al. 1988 *Infection and Immunity*, vol. 56, pp. 225–229.
Falkow, S. 1991, *Cell* vol. 65, pp. 1099–1102.
Miller, V. 1992, *ASM News* vol. 58, pp. 26–33.
Isberg, R. R. et al. 1985, *Nature*, vol. 317, pp. 262–264.
Infection and Immunity, vol. 56, 5, (May 1988), Miller et al. "Evidence for two genetic loci in *Yersinia enterocolitica* that can promote invasion of epithelial cells", 1242–1248.
Biological Abstracts, vol. 86, 2. (Jul. 15, 1988) Van Der Walt, "A comparative study of the growth of *campylobacter fetus* strains in liquid media", Abstract 15466.
Infection and immunity, vol. 57, 1, (Jan. 1989), Miller et al. "The ail locus is found uniquely in *Yershinia enterocolitica* serotypes commonly associated with disease", 121–131.
Journal of clinical Microbiology, vol. 26, 2, (Feb., 1988) Venkatesan et al. "Development and testing of invasion-associated DNA probes for detection of Shigella spp. and enteroinvasive *Escherichia coli*," 261–266.
Canadian Journal of Microbiology, vol. 21, 12, (Dec. 1975) "Ingestion and Survival of *Y. pseudotuberculosis* in HeLa cells", 1997–2007.
Cell, vol. 50 (Aug., 1987) 769–778, "Identification of Invasin: A Protein that allows enteric bacteria to Penetrate Cultured Mammalian Cells", Ralph R. Isberg et al.
Isbers et al, *Proceedings of the National Academy of Sciences USA*, 85(18): 6682–6686, (Sep. 1988) Title: Cultured mamalian cells attach to the invasin protein of *Yersinia pseudotubclosis*.
Formal et al., *Infection and Immunity*. 46(2): 465–469 (Nov. 1984). *Title:* Oral vaccination of monkeys with an invasive *Escherichia coli* K12 hybrid expression *Shigella flexneri* 2a somatic antigen.

*Primary Examiner*—Richard A. Schwartz
*Assistant Examiner*—Mary E. Mosher
*Attorney, Agent, or Firm*—Flehr, Hohbach, Test, Albritton & Herbert

[57] ABSTRACT

Novel methods and microorganisms are provided, where novel genetic mammalian cell invasive capability is imparted to a microorganism by the introduction of an exogenous inv gene. The resulting organisms are then capable of binding to mammalian cells and are transferred to the cytoplasm. Other novel genetic capabilities may be imparted to the unicellular microorganism, which may serve as a vaccine for one or more pathogens or may introduce genetic capabilities or foreign molecules into a mammalian host cell. The sequences may be used for an in vitro screen for pathogenicity.

15 Claims, No Drawings

YERSINIA INV NUCLEIC ACIDS

CROSS REFERENCE TO RELATED APPLICATIONS

This application is a continuation of application Ser. No. 07/559,904, filed Jul. 30, 1990, abandoned, which is a continuation-in-part of application Ser. No. 07/340,375, filed Apr. 19, 1989 which is a continuation-in-part of application Ser. No. 06/761,222, filed Jul. 31, 1985, abandoned application Ser. No. 07/559,904 claims priority to International Application No. PCT/US90/02131 filed Apr. 18, 1990.

INTRODUCTION

1. Technical Field

The field of this invention concerns compositions related to invasive capability of microorganisms.

2. Background

For many species of microorganisms, invasion and survival within mammalian cells is central to establishing a successful host-parasite relationship. This localization within host cells may protect the microorganism to cross epithelial barriers and subsequently become systemically distributed. The precise mechanisms by which bacteria enter host tissues have been unclear. The invasive character of pathogens, while deleterious to the health and viability of host cells, does provide a mechanism for transfer of molecules and aggregates across an intact cellular membrane. Thus, if the invasive quality could be transferred to an innocuous microorganism strain, such a strain could serve as a vehicle for transporting molecules of interest into the cytoplasm and organelles of host cells.

There is a further consideration in that the microorganism could provide for the transfer of genetic material into the mammalian host cell. In this manner, novel genetic capabilities could be imparted to the host cell. One capability of interest would be the synthesis of surface membrane proteins or envelope proteins of pathogens. These proteins would then serve as antigens to provide a strong immune response, without the host having to suffer the effects of infection by the pathogen.

Relevant Literature

The invasion of epithelial cells by *Yersinia pseudotuberculosis* is reported by Bovallius and Nilson, (1975) *Can. J. Microbiol.* 21:1997–2007 and Bolin et al., (1982) *Infect. Immun.* 37:506–512. The factors associated with Shigellae invasiveness are described by Hale et al., (1983) *Infect. Immun.* 40:340–350. Sansonetti et al., (1983) ibid 39,1392–1402 and Maurelli et al., (1985) ibid 49:164–171 describe the manipulation of the plasmid in Shigellae encoding functions essential for invasiveness.

Isberg and Falkow, (1985) *Nature* 317:262–264 and Isberg et al., (1987) *Cell* 50:769–778 describe the invasion locus of *Yersinia pseudotuberculosis.* Falkow et al., reviews of infectious diseases, 9 Supp. 5 S450-S455 (1987) describes the Yersinia gene inv. Miller and Falkow, (1988) *Inf.* and *Imm.* 56:1242–1248 describe a second invasion gene named ail (for attachment invasion locus). Miller et al., *Science* 243:916–922 describe factors involved with virulence of bacterial pathogens. Finlay et al., *Science* 243:940–943 describe invasion gene of Salmonella.

The nucleotide sequence of the *Y. enterocolitica* ail gene is described in Miller et al., (1990) *Bacteriology* 172:1062–1069. See also Miller et al., (1989) *Infect. and Immun.* 57:121–131. For a review of bacterial invasive strategies, see Finlay and Falkow (1989) 53,210–230.

SUMMARY OF THE INVENTION

Methods and compositions are provided for introducing macromolecules into mammalian host cells using substantially non-pathogenic microorganisms to which have been imparted novel invasive capability. The genetic capability of invasiveness is transferred from one microorganism host to another, whereby the recipient may now invade mammalian cells and be used as a carrier for various molecules. In this manner, molecules which cannot normally cross the cell membrane may be transported across the membrane while retaining an intact membrane and a viable host cell. In one application, the modified unicellular microorganism may be used as a vaccine by providing genetic capability for expressing surface membrane proteins or envelope proteins of various pathogens. A protocol is provided for screening invasive pathogens for the genetic sequences associated with such capabilities and transferring such genetic capabilities to non-pathogenic (innocuous) hosts.

DESCRIPTION OF THE SPECIFIC EMBODIMENTS

The subject invention provides means for introducing exogenous molecules into mammalian cell hosts employing unicellular microorganisms as the vehicle. The method involves isolating the genetic capability of invasiveness from an invasive unicellular microorganism and transferring the genetic capability to a recipient unicellular microorganism which does not naturally have the transferred gene imparting invasive capability, making any additional modifications in the modified recipient microorganism, as appropriate, and contacting mammalian cells susceptible to invasion by the modified recipient microorganism with the modified unicellular microorganism. A screening protocol is provided for identifying the genetic region associated with invasiveness, which region may be introduced directly into the recipient microorganism or may be further modified prior to introduction. The recipient microorganism may be used as a vehicle for introducing various molecules, particularly macromolecules, into a mammalian host susceptible to invasion.

The first aspect of the subject invention to be considered will be the selection protocol for identifying the genetic capability of invasiveness. An invasive unicellular microorganism is selected, the genome fragmented, either mechanically or by partial or complete digestion with one or more restriction enzymes, and the fragments Joined to an appropriate replication system for introduction into a non-invasive unicellular microorganism. The replication system may be derived from a plasmid or a virus, desirably providing for a vector having a copy number equal to or greater than one and the copy number may be 200 or greater.

The vector should neither be lethal to the host nor result in an undue reduction in viability. Desirably, the vector should provide a marker which allows for selection of recipient unicellular microorganisms which include the vector. Various markers are available, such as biocide resistance, e.g., antibiotic resistance and heavy metal resistance, genes imparting prototropy to an auxotrophic host, immunity, and the like.

The genomic fragments inserted into the vector will usually be at least about 2 kb and not more than 50 kb, generally ranging from about 5 to 20 kb. Conveniently, a viral vector may be employed which provides for selection of fragments in the desired range based on the packaging requirements. While it is not essential to select for the microorganisms which have received the vector, it is preferable to select for recipient unicellular microorganisms. Desirably, the vectors should be capable of stable episomal maintenance or integration into the genome. Where integration is involved, amplification of the gene is desirable.

The genome of invasive unicellular microorganisms are mechanically sheared or digested with one or more restriction enzymes, either partially or completely, to provide fragments in the range of about 2 to 20 kbp. The fragments are then inserted into an appropriate vector, such as a vital vector, e.g., cosmid, or plasmid vector, e.g., pBR322. Non-invasive unicellular microorganisms are transfected or transformed with the vectors and modified organisms are selected by means of a marker, e.g., antibiotic resistance. The desired clones are then enriched by the following procedure.

The surviving organisms are cloned, suspended in an appropriate nutrient medium and introduced onto confluent layers of invasive susceptible mammalian cells. The cells are allowed to incubate for a sufficient time, usually at least about 1 hour, and less than about 12 hours, conveniently from about 2 to 6 hours, under conditions which maintain viability of the cells. The monolayer is then stringently but carefully washed under conditions which remove nonadherent recipient microorganisms, so that only adherent microorganisms remain bound to the mammalian cell monolayer. The internalized cells are then released from the monolayer by treatment with a mild detergent, e.g., a nonionic detergent, generally at a concentration in the range of about 0.1 to 2%, more conveniently about 0.5 to 1.5%, in an aqueous medium. Any mild technique which allows for the viability of the microorganism with release of the microorganism cells from the mammalian cells may be employed. The released microorganism cells are then expanded and cloned.

Transposon mapping may be employed for identifying the transposon insertions which destroy invasive capability. In this manner, the structural gene with its associated regulatory signals can be mapped to a particular site on the fragment. Other techniques involve employing partial digestions, cloning and screening for invasive capability, followed by sequencing and identifying specific sequences associated with transcription and translation as indicative of the structural gene and its associated regulatory signals.

If desired, the regulatory signals, particularly the transcription initiation signal, may be modified by the addition or substitution of the native transcriptional initiation region with a transcriptional region associated with a different gene. In this way, one can provide for low or high levels of constitutive or inducible expression of the DNA sequence encoding for invasive capability. Various transcriptional initiation regions or promoters are available, which are temperature sensitive, are inducible in the presence of various metabolites or nutrients, and the like. Therefore, a transcriptional initiation region may be employed which is regulated by the unicellular microorganism host and the invasive capability may be activated or inactivated by physically or chemically changing the environment of the microorganism host. Thus, nutrients and metabolites such as glucose, tryptophan, histidine, galactose, lactose, may be employed to induce or repress the expression of the invasive gene (inv). The inducible transcriptional regulatory region may be selected in accordance with the mammalian host, depending upon whether the coinducer or corepressor is naturally found in the mammalian host or can be administered to the host.

Constructs may then be prepared which may be used for introducing invasive capability into an appropriate unicellular microorganism host. Depending upon the purposes for invasiveness, a wide variety of bacterial or eukaryotic microorganism hosts may be employed. The subject method provides for introduction of DNA capability into a mammalian cell where the unicellular microorganism is employed as the vehicle for introduction of the DNA capability into a mammalian cell. For example, a shuttle vector may be provided in the invasive microorganism host which has the capability for replication in the mammalian cell as well as the unicellular microorganism, where the shuttle vector may exist as an episomal element or become integrated into the mammalian cell genome. In this manner, unicellular hosts for cloning may be used directly for the transfer of DNA into a mammalian cell host with high efficiency. Thus, a wide variety of genetic capabilities can be introduced into mammalian hosts, for example, the expression of lymphokines, hormones, enzymes, surface membrane proteins, and the like, such as interferons, interleukins, growth factors, hydrolases, oxidoreductases, receptors, antibodies, histocompatiability antigens, etc.

A second manner in which the invasive organism may be used is as a vaccine. For this purpose, in addition to the invasive genetic capability, genes encoding for surface membrane proteins, capsid proteins, or envelope proteins, singly or in combination, may be introduced into the invasive modified microorganism host for injection into a mammal to induce an immune response. The genes encoding for the antigens may be obtained from a wide variety of pathogens, including viruses, prokaryotes, e.g., bacteria, eukaryotes, e.g., fungi, protists, or the like, or such intermediate species as chlamydia. In many cases, the gene of interest is known and available or may readily be isolated. Where not known, the techniques employed for identifying specific structural genes can be employed for identifying the genes coding for the desired antigen.

A third manner in which the invasive organism may be used is as a vehicle for the introduction of molecules, particularly macromolecules, into a mammalian cellular host, either in vitro or in vivo. For example, cytotoxic resistance provided by an enzyme could be transferred into cells or a cytotoxic agent, e.g., aminoglycosides, hybritoxins, etc., non-cytotoxic to the microorganism, could be introduced into mammalian cells. Dyes or other contrast agents could be introduced into the cells for visualization of cell features. Labelled antibodies could be introduced into the cells to define the location of particular antigens. Invasion proteins may be used to introduce particles, such as colloidal particles, liposomes, slowly degrading or slow release particles, cells, or the like, where the particles may include drugs, dyes, nucleic acid, antibodies, or other substances which may have physiological activity. The invasion proteins may be bound non-diffusibly to the particles, either covalently or non-covalently. The literature has numerous examples of commercially available cross-linking agents for joining proteins to other proteins, sugars, synthetic organic polymers, both addition and condensation, and the like.

Invasion proteins may also be used to bind mammalian cells to a surface. Thus in cell cultures, cells may be reversibly bound to a surface, isolated or otherwise be manipulated. Other uses will also be apparent.

A large number of mammalian replication systems and vectors are available, particularly viral replication systems, such as SV-40, adenovirus, bovine papilloma virus, etc. See, for example, Southern and Berg, *J. Mol. Appl. Genet.* (1982) 1:327–341; and Mulligan and Berg, *Proc. Natl. Acad. Sci. USA* (1981) 78:2072–2076, which are incorporated herein by reference.

One technique would involve employing antisera from a mammalian host who had suffered, particularly was undergoing infection, by the pathogen of interest. The pathogen in culture could be lysed and immunoprecipitated with the antisera from the mammalian host and electrophoresed. A cDNA or genomic library could be prepared from the pathogen. By at least partially sequencing the immunoprecipitated proteins, amino acid sequences could be identified, which could be translated into probes. The probes could then be used for screening the library and identifying sequences complementary to the probes. Once sequences which hybridize to the probes have been identified, where the regulatory sequences are recognized by a prokaryotic host, the prokaryotic host may be transformed with the sequence and the expression product identified. Where the expression of the structural gene is regulated by sequences which are not recognized by prokaryotic hosts, then some manipulation will be required in identifying the sequence coding for the particular antigen and inserting the sequence into an appropriate expression vector. A large number of expression vections exist and various techniques are available for tailoring the structural gene to remove superfluous DNA sequences, particularly 5' to the structural gene- Techniques such as resection with Bal31, primer repair, and in vitro mutagenesis to introduce a convenient restriction site, have all been used successfully.

Antigens of interest may come from a wide variety of sources, such as bacteria, such as Bordatella, Salmonella, Neisseria, Pneumococcus, Shigellae, Yersinia, Cholera, Meningococcus, Listeria, Mycobacterium, etc.; viruses, such as HTLV-I, -II, and -III, FeLV, HSV-1 and -2, Adenovirus, Varicella, Vaccinia, Hepatitis, Influenza, Measles, Rubella, Smallpox, Typhoid, Yellow Fever, etc. fungi, such as Candida, Microsporum, Tricpohyton, Arthroderma, cryptococcus, Blastomyces, Histoplasma, Coccidroides, Paracoccidroides, Aspergillus, Phycomycetes, Sporotorax, Epidermophyton, etc. other pathogenic microorganisms, such as Chlamydia, Giardia, etc.

The organisms may be administered in any convenient form as a vaccine. Normally, physiologically acceptable carriers will be employed, such as deionized water, phosphate buffered saline (PBS), aluminum hydroxide, sugar or the like. Usually, the dosage will be determined empirically; about $10^4$ to $10^{10}$ cells will be administered to a human host, with proportionate administration based on size to other mammalian hosts. Generally, there will be a first administration, followed by one or more administrations at two to six week intervals. The particular amount administered will depend upon a number of factors, such as the viability of the invasive microorganism in the host, the concentration of the antigen on the surface of the pathogen, the number of different antigens which are present, the level of immune response to the particular antigen(s), and the like. Administration may be orally, by injection, intravenously, intraarterially, subcutaneously, intraperitoneally, etc. The manner of administering live vaccines is well established and may be found in such texts as Basic and Clinical Immunology, eds. Stites, Stobo. Fudenberg and Wells. 4th ed. Lange Medical Publications, Los Altos, CA, 1982.

The gene coding for the invasive genetic capability may come from any convenient source. A significant number of organisms are known to be capable of invasion, such as Yersinia, Chlamydia, *Legionella pneumophila, Listeria monocytogenes, Mycobacterium tuberculosis, Mycobacterium leprae, Salmonella typhosa, Salmonells typhimurium*, enteropathogenic *E. coli* (EPEC strains), *Brucella abortus, Cryptococcus neoformans, Histoplasma capsulation, Candida albicans, Tripanosoma cruze, Toxaplasma gondi, Leishmania donovani*, etc. Thus, the organisms may be bacterial, fungal or protozoan. Preferred organisms will be those which provide a single gene which results in invasive capability. The affinity for the mammalian host receptor should be at least about 0.1. Of particular interest are Yersinia and Salmonella which are demonstrated in the Experimental section as paradigmatic of invasive organisms.

Genes derived from Yersinia species, particularly *Y. pseudotuberculosis* and *Y. enterocolitica* provide a gene referred to as inv with a phenotype INV, while the latter provides the additional gene ail with a phenotype AIL. *Salmonella typhimurium*, and group A meningococci, are found to have analogs to the inv and/or ail genes. The inv gene is found not to be homologous to ail. While both genes provide for invasiveness, the host range of ail is different from the inv genes. These ail genes are found to be chromosomal, rather than present on plasmids.

The non-invasive host which is modified to become invasive may be prokaryotic or eukaryotic and will be selected depending upon its ultimate purpose. Where the organism is to be the vehicle for transfer of DNA into mammalian cells in culture, then any convenient organism may be employed, particularly one which may be used for cloning of the DNA to be transferred. Therefore, many of the strains of *E. coli*, e.g., K12, may be employed as the recipient microorganism which is modified to become invasive. Where the modified microorganism host is to be employed as a vaccine, the host will normally be selected so as to be innocuous (nonpathogenic), to be capable of being viable extracellularly for an extended period of time, preferably at least about 3 days in the vaccinated host, and to be subject to ready clearance in the vaccinated host. Desirably, the modified recipient microorganism will be free of pyrogens, toxins, or other disease symptom causing factors. By innocuous is intended that regardless of the dose or route, no disease will be observed with an immunocompetent host. While pathogenic microorganisms may be employed, particularly attenuated pathogenic microorganisms, these are not preferred, since there is a possibility of reversion to pathogenicity. Microorganism hosts which may be used for modification to invasive capability include besides *E. coli*, members of the genus Staphylococci, Pneumococci, Streptococci, e.g., mutants, Neisseria, e.g., catarrhalis, Veillonella, Lactobacilli, Corynebacteria, Clostridia,, Hemophilic bacilli, Bacteroides, Actinomycetes, Spirochetes, Mycoplasma, etc.

The manner in which the genetic capability for invasiveness is introduced into the recipient microorganism may be any of the convenient techniques including transformation, e.g., calcium precipitated DNA, transfection, transduction, conjugation, fusion, etc. Applicable techniques may be found in Maniatis et al., A Laboratory Manual, Cold Spring Harbor Laboratory, Cold Spring Harbor, New York, 1982. As already indicated, a marker will normally be present which allows for selection of those microorganisms which have received the invasive genetic capability. The organisms may then be grown in an appropriate nutrient medium and used as appropriate.

The invasive microorganisms may be used to prepare antisera for passive immunization. Thus, γ-globulin could be prepared which has antibodies to a broad spectrum of pathogens and for strains of a particular pathogen. The γ-globulin may be isolated and purified from serum by ammonium sulfate precipitation and fractionation according to known techniques. Administration to a mammalian host will generally be in amounts of 50 to 500 mg/kg of host in any physiologically acceptable carrier. Administration will usually be by injection, e.g., intravenously. The modified recipient microorganism may also be used in assays for detecting the presence of antibodies to the antigens foreign to the modified microorganism or the antigens themselves. They also may find use in competing with the invasive microorganisms so as to be useful for therapy.

In addition, the subject microorganisms may be used for expression of proteins expressed by the inv gene. Particularly, by having high copy number vectors, the modified foreign microorganisms may be harvested, lysed and the inv antigen isolated by conventional ways, e.g., affinity chromatography, electrophoreses, chromatography, etc.

Sequences encoding all or a portion of the invasion genes may be used for diagnosing pathogenicity or virulence. Two fragments of interest from the ail locus are 0.9kbp AvaI-ClaI fragment from the plasmid pVM103 and a 1.2kb ClaI-AvaI fragment from the same plasmid or fragments thereof of at least about 50 bp, preferably at least about 100 bp or extensions thereof including the entire ail coding region or locus. In conjunction with the ail probes, a probe referred to as Inv-Ent may be employed, which is a 3.6 kb ClaI fragment obtained from pVM101, or 50 bp fragment thereof, preferably at least a 100 bp fragment thereof. The 3.6 kb fragment comprises most of the inv gene from *Y. enterocolitica* in addition to adjacent sequences.

Alternatively, a probe referred to as Inv-PSTB may be employed which is a 2.4 kb ClaI-XhoI fragment obtained from pRI203. Isberg et al., Cell 50:769–778 (1987). Of particular interest is the use of all specific sequences for detecting pathogenicity. In pathogenic strains multiple copies of sequences having homology to AIL-B are frequently observed. With the Inv probes, a size pattern is observed when the microorganisms DNA is cleaved with EcoRV. These strains may be divided into types I, II, I/II, III, IV and V by the size of fragments observed. This restriction enzyme cuts once within the Inv-Ent probe, but does not cut within the AIL-B or C probes. The various types are defined in the Experimental section where, types I and I/II were found to be pathogenic, while the remaining types were non-pathogenic, with a strong correlation.

To enhance the invasive phenotype, bacteria are grown in an atmosphere of about 1% oxygen by maintaining a gaseous source of oxygen at that level. This may be contrasted with young cultures of laboratory grown cells (which are typically in the mid-log phase of growth) or overnight cultures (which are typically in the stationary phase of growth). By growing cells in 1% oxygen the invasive phenotype is encouraged and the resulting cells may be more readily screened for the presence of the mRNA encoding for invasiveness, for use as vaccines or for studying the mechanism of the regulation of the invasive phenotype.

The following examples are offered by way of illustration and not by way of limitation.

EXAMPLES

Enrichment for Invasive Phenotype

A cosmid bank was constructed (Hohn, *Methods in Enzymology* (1979) 68:229–309; Koomey et al., *Proc. Natl. Acad. Sci. USA* (1982) 7.9:7881–7885) by ligating a size-fractionated Sau3AI digest of chromosomal DNA isolated from *Y. pseudotuberculosis* strain YPIII (p−) (Bolin and Wolf-Watz, *Infect. Immun.* (1984) 43:72–78) into the BamHI site of pREG153 (available from Dr. R. Gill) a cosmid cloning vehicle that encodes resistance to ampicillin and is further characterized by its low copy number (5–8). Aliquots of the ligation mixture were packaged in vitro (Enquist and Sternberg, *Methods in Enzymology* (1979) 68:281–298) into phage lambda heads with an extract prepared from MMSA345 (available from Dr. F. Stahl) and then infected into *E. coli* K12 strain HB101 (Maniatis et al., A Laboratory Manual), selecting for ampicillin-resistant transductants. Pooled bacteria were grown overnight in culture, washed twice in sterile PBS and resuspended to a density of $5\times10^8$ bacteria ml$^{-1}$. The washed bacteria (2 ml) were then introduced onto a confluent monolayer containing $1\times10^7$ HEp-2 cells grown in RPMI1640 medium (Irvine Biologicals), and incubated for 3 hours at 36° C. in a 5% $CO_2$ atmosphere. Monolayers were then washed 10 times with sterile PBS to remove non-adherent bacteria. Bacterial clones remaining associated with the monolayer were released with 1% Triton X-100 in deionized water, and plated for individual colonies on bacteriological medium.

Screen for Invasive Cultures

Saturated cultures of the transformed bacteria were grown at 28° C., washed twice in PBS and resuspended to a concentration of $3\times10^8$ bacteria ml$^{-1}$. Aliquots (50 $\mu$l) of each strain were added to monolayer cultures of HEp-2 cells seeded at a concentration of $2\times10^5$ animal cells per microtiter well (24 well, Falcon 3047 microtiter dishes) in RPMI1640 medium. Bacteria were centrifuged onto the monolayer at $600\times g$ (Devenish and Schiemann, *Infect. Immun.* (1981) 32:48–55), and the infected cultures were incubated at 36° C. for 3 hours in 5% $CO_2$ atmosphere, to allow binding and invasion of bacteria. Non-adherent bacteria were removed from the monolayer by washing three times with sterile PBS, and RPMI medium containing 40 $\mu$g ml$^{-1}$ gentamicin (Sigma Chemical) was added to each microtiter well. The incubation was continued at 36° C. for 2 hours in the presence of the antibiotic, before washing the monolayers twice more with PBS. Internalized bacteria were then released from the monolayers by the addition of 1% Triton X100 and titered on L agar plates (Miller, *Experiments in Molecular Genetics,* Cold Spring Harbor Laboratory, Cold Spring Harbor, New York, (1972)). The following table indicates the results.

TABLE 1

Enrichment Procedure Yields *E. Coli* Strains That Invade Cell Culture Monolayers

| Strain | % Invasion[d] |
|---|---|
| YPIII(p⁻)[a] | 9.0 |
| HB101[b] | 0.005 |
| HB101(pINVA2)[c] | 8.3 |
| HB101(pINVA7) | 7.9 |
| HB101(pINVG10) | 8.7 |
| HB101(pRI203) | 9.2 |

[a] *Yersinia pseudotuberculosis* strain (Bolin et al. supra).
[b] *E. coli* K12 strain HB101.
[c] HB101 harboring cosmids that are denoted in parenthesis).
[d] Percentage of bacteria added to HEp-2 monolayers that resist treatment by gentamicin.

It was found that 12 of the 22 candidate strains that survived the enrichment were invasive, based on the above. It is noteworthy that the efficiency of escape from gentamicin treatment, which may be equated with bacterial invasion, was similar to that found for the *Y. pseudotuberculosis* strain used as the DNA donor.

To determine if isolated bacterial derivatives could invade cultured animal cells, ultrathin sections of monolayer cells exposed to several of the bacterial strains were analyzed by electron microscopy (Horwitz, *J. Exp. Med.* (1983) 158:1319–1331). Tissue culture cells (Falcon 3046, 6 well dishes) seeded with $8 \times 10^5$ HEp-2 cells in RPMI 1640 were incubated in the presence of $6 \times 10^{-7}$ bacteria for 3 hours at 36° C. Monolayers were then washed 10 times with PBS and incubated for 10 minutes at 37° C. in the presence of PBS containing 0.1 mM EDTA. The monolayers were gently washed once more with PBS in the presence of EDTA, suspended in 1 ml of PBS, and pelleted at 600 xg for 10 minutes. The cell pellets were successively fixed with 2% glutaraldehyde and 2% osmium tetroxide in 0.1M cacodylate buffer (pH 7.4), before staining with uranyl acetate. Samples dehydrated in ethanol were embedded in Spurrs (Polysciences), thin sectioned, stained successively with 1% uranyl acetate and lead acetate (Reynolds, *J. Cell. Biol.* (1963) 17:208–213), and visualized with a Phillips 201c electron microscope. An *E. coli* K12 HB101 strain is unable to enter HEp-2 cells. In contrast, the same bacterial strain harboring an intact inv locus showed a large number of bacteria associated with the animal cell. These bacteria appeared to be both bound to the outside of the cell as well as present within large endocytic vesicles. Furthermore, when *E. coli* HB101 cells were employed which harbor the pRI203 plasmid with an intact inv locus, invasion was observed, whereas the same bacteria which harbored the plasmid pRI203.14::Tn5, which has a Tn5 insertion mutation in the inv locus were compared, no invasion was observed. Therefore, invasiveness is only observed with a functionally intact inv locus. The number of intracellular bacteria had substantially diminished and the invaded cells remained viable.

The locus of the inv gene was established as follows. One plasmid, pINVA2 was analyzed by causing a series of Tn5 insertion mutations in the cosmid DNA, taking the precaution that each mutation analyzed was the result of an independent event. Mutations were induced by the kanamycin-resistance transposon Tn5 via transposition from λb221rex::Tn5 c1857Oam23Pam80 onto pINVA2 according to the method of deBruijn and Lupski, *Gene* (1984) 27:313–149. To select for insertions onto the cosmid, kanamycin-resistant colonies were pooled together and infected lytically with μlac5 imm21cts. The resulting lysate was used to transduce HB101 to simultaneous kanamycin- and ampicillin-resistance- Such transductants contained insertions of Tn5 at random sites on the cosmid. Several hundred such transductants were assayed for invasiveness as described previously, and the map position of 20 mutants that eliminated invasiveness and 20 insertions that had no effect on the invasive phenotype were determined. In order to ensure that each insertion was independent, the physical location of no more than one mutation from each pool was analyzed. The sensitivity to insertion inactivation of the invasive phenotype was mapped to a contiguous 3.2 kb region, which region was shown to code for a single large protein which was indicated as being 108 kdal by electrophoresis using myosin, β-galactosidase and phospholipase G as standards.

Demonstration of Two Genetic Loci for Invasion of Epithelial Cells in *Y. Enterocolitica*

Materials and Methods

Bacterial Strains and Tissue Culture Cells

*Y. enterocolitica* 8081c (Portnoy et al., *Infect Immun.* (1981) 31:795–782) and *E. coli* HB101 were maintained at −70° C. in Luria broth (LB) medium containing 25% (vol/vol) glycerol or on LB agar plates. Antibiotics were used at the following concentrations: ampicillin, 50 μg/ml; chloramphenicol, 50 μg/ml; kanamycin, 40 μg/ml. Hu/nan laryngeal epithelium (HEp-2), Madin-Darby canine kidney (MDCK), and Chinese hamster ovary (CHO) cells were maintained and prepared for the invasion assay as previously described (Finlay and Falkow, UCLA *Symp. Mol. and Cell. Biol.* (1987) 64:227–243). Human endometrial (HEC-1B) tissue culture cells were maintained and prepared for invasion assays in the same manner as HEp-2 cells, with the exception that 10% fetal calf serum was used in the HEC-1B tissue culture medium. *Y. enterocolitica* 8081c and *E. coli* HB101 carrying recombinant plasmids with *Y. enterocolitica* invasion genes were grown at 28° C. with aeration for 12 to 18 hours in LB. HB101 carrying the type I pilus clone PSH2 was grown in LB containing chloramphenicol at 37° C. without aeration (Orindorff and Falkow, *J. Bacteriol.* (1984) 159:736–744). HB101 carrying the PAP pilus clone pPAP5 (Hindberg et al., *EMBO J.* (1984) 3:1167–1173) was grown on tryptic soy agar plates containing ampicillin at 37° C. HB101 carrying the X-adhesinAFA-1 clone pIL14 (Labigne-Roussel, *Infect Immun.* (1984) 46:251–259) was grown on LB agar plates containing epicillin at 37° C.

Nucleic Acid Preparation and Analysis

High-molecular weight chromosomal DNA was isolated as previously described (Hull et al., *Infect Immun.* (1981) 33:933–938). Plasmid DNA was purified by the alkaline lysis method (Maniatis et al., (1982) Molecular Cloning=A Laboratory Manual, CSHL, Cold Spring Harbor, New York). DNA restriction enzymes and bacteriophage T4 DNA ligase were purchased from Bethesda Research Laboratories, Inc. Calf alkaline phosphatase was purchased from Pharmacia, Inc. Restriction enzymes, ligase, and phosphatase were used according to the instructions of the manufactures.

Invasion Assay

Bacteria ($2 \times 10^7$) were added to each well of a 24-well microdilution dish which had been seeded with tissue culture cells the previous day as previously described (Finley and Falkow, (1987) supra). The microdilution plates were centrifuged for 10 minutes at ambient temperature at 162xg and then incubated in a 5% $CO_2$ incubator at 37° C. After 3 hours, the tissue culture medium was removed and the cells were washed three times with phosphate-buffered saline to remove nonadherent bacteria. Fresh tissue culture medium containing 100 μg of gentamicin per ml was then added, and the plates were reincubated as described above. After 90 minutes, the medium was removed and the cells were washed twice with phosphate-buffered saline to remove the gentamicin. The tissue culture cells were then lysed to release intracellular bacteria by adding 0.2 ml of 1% Triton X-100 to each well. After 5 minutes, 0.8 ml of LB was added; the final concentration of Triton X-100 was 0.2%. The suspension was then diluted and plated on the appropriate bacteriological medium to determine viable counts. Viable counts of the initial bacterial culture were also determined. Results are expressed as follows: % invasion=100×(the number of bacteria resistant to gentamicin/the number of bacteria added).

The total number of cell-associated bacteria was determined in the same way as was the number of intracellular bacteria, with the following exception: after incubation of the bacteria with the monolayer for 3 hours, the monolayer was washed five times with phosphate-buffered saline. The monolayer was then disrupted with 1% Triton X-100 as described above, and viable counts were determined.

Construction of a Chromosomal DNA Library of Y. enterocolitica

High-molecular-weight chromosomal DNA from Y. enterocolitica 8081c was partially digested with the restriction enzyme Sau3A as previously described (Maniatis et al., (1982) supra). Fragments 7 to 10 kilobase pairs in size were isolated by sucrose gradient fractionation and ligated into pBR322 that had been digested with BanHI and treated with calf alkaline phosphatase. The resulting ligated DNA was used to transform competent E. coli HB101 cells. E. coli HB101 transformants carrying recombinant plasmids were selected on LB agar plates containing ampicillin.

Stained Samples and Electron Microscopy

Samples of invasion assays were prepared and stained for electron microscopy as previously described (Isberg and Falkow, Nature (1985) 317,262-264).

Tn5 Mutagenesis

Strains bearing insertions of transposon Tn5 into recombinant plasmid pVM102 were isolated as previously described (deBruiJn and Lupski, Gene (1984) 27:131-149).

RESULTS

Cloning Invasion Genes From Y. enterocolitica

Y. enterocolitica 8081c (serotype 08) was used, which had been isolated from a patient with septicemia, as our prototype strain (Portnoy et al. (1981) supra). Strain 8081c lacks the 47-megadalton virulence-associated plasmid, as well as any other plasmid, yet is still able to invade HEp-2 cells as efficiently as is the plasmid-containing strain. This suggests that, as in Y. Pseudotuberculosis, the invasion determinants are chromosomally encoded. Consequently, to clone the genes from Y. enterocolitica 8081c which were involved in invasion, a library of chromosomal DNA from strain 8081c, was first constructed in the plasmid vector pBR322. This library was used to transforms, the normally nonadherent and noninvasive E. coli HB101. Adhesive and invasive clones were selected by pooling the resulting transformants and infecting a monolayer of HEp-2 tissue culture cells as described above in Materials and Methods. After 3 hours of incubation, the monolayer was washed 15 times with phosphate-buffered saline and then lysed with 1% Trition X-100 to release any intracellular or adherent bacteria. The suspension was then spread on LB plates containing ampicillin. Gentamicin was not used during this enrichment procedure because we felt that invasion may be a two step process involving at least two loci, one for attachment and a second for invasion. If this were the case, the attachment factor would be a prerequisite for identifying a recombinant strain carrying the invasion gene.

Clones from the enriched population were then tested individually in the invasion assay. Approximately 50% of the clones that survived the enrichment were able to invade HEp-2 tissue culture cells to some degree.

E. coli HB101 transformants expressing an invasion phenotype fell into two classes (Table 2). The first class, represented by clones 6, 8, and 9, demonstrated a high level of invasion similar to that of wild-type Y. enterocolitica 8081c and 800- to 1,400-fold higher than the background level seen with E. coli HB101. The second class, represented by clones 3 and 7, demonstrated a relatively low level of invasion, which was nevertheless 40- to 100-fold higher than that of HB101.

TABLE 2

Relative Invasion of Y. enterocolitica Clones Into HEp-2 Cells[a]

| Infecting Strain | % Invasion |
|---|---|
| Y. enterocolitica 8081c | 26.8 ± 3.6 |
| E. coli HB101 | 0.0075 ± 0.0035 |
| HB101(pBR322-8081c) (clone 3) (= pVM103) | 0.82 ± 0.24 |
| HB101(pBR322-8081c) (clone 7) (= pVM102) | 0.37 ± 0.19 |
| HB101(pBR322-8081c) (clone 6) (= pVM101) | 6.2 ± 2.1 |
| HB101(pBR322-8081c) (clone 8) | 10.8 ± 0.1 |
| HB101(pBR322-8081c) (clone 9) | 6.9 ± 0.32 |

[a]Strains were used to infect a monolayer of HEp-2 tissue culture cells as described in Materials and Methods. Values are the averages of duplicate samples, with the ranges indicated, and reflect similar results from several experiments.

Characterization of Y. enterocolitica Invasion Clones

Isolation and characterization of plasmid DNA from clones 6, 8, and 9 indicated that they all contain the same fragment of Y. enterocolitica DNA. The recombinant plasmid from clone 6 was called pVM101. Southern hybridization analysis indicated that plasmid pVM101 shares homology with the inv gene from Y. pseudotuberculosis and thus is a clone of the Y. enterocolitica inv locus. The homology shared with Y. pseudotuberculosis inv is not observed at the restriction map level.

Isolation and characterization of plasmid DNA from clones 3 and 7 indicated that they have overlapping inserts of Y. enterocolitica DNA. These two plasmids were renamed pVM103 and pVM102, respectively. Plasmids pVM102 and pVM103, while they share homology with each other, are not homologous to pVM101, as demonstrated by both Southern hybridization and restriction map analysis and thus probably represent a new locus involved in invasion.

A high proportion of E. coli HB101 recombinant cells carrying either pVM102 or pVM103 adhered to the HEp-2 cell monolayers. This raised the possibility that the low level of invasion observed with the quantitative invasion assay reflected a small proportion of adherent bacteria that were protected from the gentamicin treatment. To determine whether bacteria were actually being internalized, electron microscopy was performed on samples of HEp-2 cells infected with HB101(pVM102). Bacteria were frequently found in very close association with eucaryotic cell membranes. A small number of intracellular bacteria were also observed suggesting that pVM102 confers a phenotype of adhesion and low-level invasion of HEp-2 tissue culture cells on E. coli HB101. Electron-dense eucaryotic structures resembling coated pits were frequently found in association with attached bacteria, regardless of whether the bacteria were Y. enterocolitica 8081c or E. coli HB101 carrying either of the recombinant plasmids, pVM101 or pVM102. Whether or not these structures play a role in microbial attachment or entry or both is not known at this time. Strain 8081c, unlike HB101 carrying either pVM101 or pVM102, is seen almost exclusively intracellularly after 3 hours of infection. This observation would suggest either that there are other gene products directly involved in invasion or that the gene products encoded by pVM101 and pVM102 do not function as effectively in an E. coli background. Electron microscopy of negatively stained cultures of HB101 pVM102 and pVM101 do not indicate the presence of any pilus-like structures on the surface of these bacterial cells.

The ability of E. coli HB101 carrying several cloned virulence-associated adhesions to invade HEp-2 cells was tested (Table 3) to determine whether adherence alone promoted a low level of invasion. HB101 harboring recombinant plasmids encoding type 1 pili (Orndorff and Falkow, (1984) supra), PAP pili (Lindberg et al., (1984) supra), or X-adhesin AFA-1 (Lahyne-Roussel et al., (1984) supra) was cultured in such a way as to maximize expression of the adhesin. While all three of these adhesions promoted adherence of E. coli HB101 to HEp-2 cells, as determined by examination of Giemsa-stained cover slips and by quantitative assay, the presence of type 1 pill, PAP pill, or X-adhesin did not confer an invasive phenotype of E. coli HB101 (Table 3), nor were coated pits seen associated with the adherent bacteria. This result indicates that the invasive phenotype of HB101(pVM102) is a specific property of this recombinant strain and not a manifestation of simple adhesion.

TABLE 3

Effect of Adhesion on Invasion[a]

| E. coli Strain | % Invasion | Adhesin Type |
|---|---|---|
| HB101(pBR322) | 0.015 ± 0 | —[b] |
| HB101(pVM102) | 0.770 ± 0.03 | — |
| HB101(pSH2) | 0.067 ± 0.001 | Type 1 pilus |
| HB101(pPAPS) | 0.020 ± 0 | PAP pilus |
| HB101(pIL14) | 0.007 ± 0.001 | X-adhesin |

[a]Strains were used to infect a monolayer of HEp-2 tissue culture cells as described in Materials and Methods. Values are the averages of duplicate samples, with the ranges indicated, and reflect similar results from several experiments.
[b]—, Not known.

Localization of the Invasion Locus of pVM102

Insertions of transposon Tn5 insertions were mapped, and their invasive phenotypes were determined. Six insertions that eliminated invasion were clustered to the right of the unique ClaI site. Insertion mutants defective for invasion were found only in this region, suggesting that there is only one region on this plasmid that is responsible for both adherence and invasion. There are only approximately 650 base pairs between the Inv+ insertions flanking the Inv— insertions, suggesting that this region contains a very small gene(s). We have designated this region ail for attachment-invasion locus.

Invasion of Other Tissue Culture Cell Lines

One possibility for the role of ail gene(s) is that it defines target cell types other than those defined by inv thus giving Y. enterocolitica a different range of target host cells than might result from the presence of inv alone. To test this hypothesis, invasion by HB101 carrying either of the cloned Y. enterocolitica invasion loci, inv or ail, was examined in several cell lines (Table 4). All cell lines were invaded by Y. enterocolitica 8081c, although to various degrees. Plasmid pVM101 promoted only a low level of invasion of MDCK cells by HB101. Plasmid pVM101 caused HB101 to invade all tested cell lines, except the MDCK cells, at a relatively high level. HB101(pVM102) invaded the tested cell lines to different degrees. The recombinant strain HB101(pVM102) did not invade MDCK cells, invaded HEp-2 and HEC1B cells at a low level, and invaded CHO cells at a high level. This suggests that cell lines may vary in their capacity to phagocytize bound bacteria and that this variability can be specific to the invasion factor expressed by the bacteria.

TABLE 4

Invasion of Tissue Culture Cell Lines by Y. enterocolitica and Y. enterocolitica Bacteria in Tissue Culture Cell lines[a]

| Infecting Strain | % Invasion Of: | | | |
|---|---|---|---|---|
| | HEp-2 | MDCK | CHO | HEC1B |
| 8081c | 26.8 ± 3.6 | 0.93 ± 0.07 | 20.4 ± 5.9 | 124.3 ± 5.0 |
| HB101 (pBR322) | 0.0075 ± 0.0035[b] | <0.0001 | 0.08 ± 0.01 | 0.005 ± 0.001 |
| HB101 (pVM101) | 6.2 ± 2.1 | 0.015 ± 0.0015 | 15.2 ± 1.3 | 19.1 ± 2.4 |
| HB101 (pVM102) | 0.37 ± 0.19 | <0.0001 | 12.7 ± 0.2 | 5.5 ± 1.2 |

[a]Strains were used to infect monolayers of the tissue culture cell lines as described in Materials and Methods. Values are the averages of duplicate samples, with the ranges indicated, and reflect similar results from several experiments.
[b]From infection of HEp-2 with HB101. Results were similar for HB101 and HB101 (pBR322).

The total number of cell-associated bacteria, both attached and intracellular, was also determined (Table 5). Although HB101 (pVM102) invaded HEp-2 cells at only a low level, it bound to HEp-2 cells as well as if not better than it did to CHO cells and to a slightly higher degree to both these cell lines than did HB101(pVM4101) (Table 5). Indeed, there is no correlation between number of bacteria bound and number of bacteria internalized, suggesting that the interaction of these bacteria with tissue culture cells that leads to internalization involves more than just attachment to the cell surface.

TABLE 5

Percent Cell-Associated Bacteria in Tissue Culture Cell Lines[a]

| Infecting Strain | % Invasion Of: | | | |
|---|---|---|---|---|
| | HEp-2 | MDCK | CHO | HEC1B |
| 8081c | 67.0 ± 4.0 | 15.0 ± 1.7 | 51.0 ± 5.0 | 104.0 ± 53 |
| HB101 (pBR322) | 11.0 ± 1.7 | 0.34 ± 0.07 | 3.6 ± 0.71 | 7.4 ± 2.3 |
| HB101 (pVM101) | 34.0 ± 2.0 | 4.4 ± 0.05 | 26.0 ± 3.0 | 58.0 ± 5.2 |
| HB101 (pVM102) | 43.0 ± 0.2 | 4.2 ± 0.2 | 37.0 ± 4.0 | 10.0 ± 1.6 |

[a]Strains were used to infect monolayers of the tissue culture cell lines as described in Materials and Methods. Values are the averages of duplicate samples, with the ranges indicated, and reflect similar results from several experiments.

The above results demonstrate that the invasion loci, designated inv, allows a uniformly high level of invasion in several tissue culture lines and the inv gene of *Y. pseudotuberculosis* and *Y. enterocolitica* are homologous. The second invasion locus of *Y. enterocolitica* is ail. Bacteria containing ail exhibit several invasion phenotypes, depending upon which cell line is infected. ail promotes a high level of invasion of CHO cells and a low to moderate level of invasion of other cell lines (HEp-2 and HEC-1B) but allows no invasion of MDCK cells. The recombinant plasmid pVM102 strongly promotes adherence of *E. coli* HB101 to many cell lines, including those cell lines for which it does not promote efficient invasion (e.g., HEp-2). Although *E. coli* (pVM102) adheres as well to HEp-2 cells as to CHO cells, more intracellular bacteria are found in CHO cells. The phenotypes of attachment and invasion which are associated with the presence of pVM102 appear to be encoded by fewer than 650 bp of DNA.

Screening of Yersinia for Pathogenesis Materials and Methods

Bacterial Strains and Tissue Culture Cells

Bacterial strains were maintained at −70° C. in Luria broth (LB) medium containing 25% (vol/vol) glycerol, or on LB agar plates. Yersinia strains obtained from a variety of sources were tested for invasion in the tissue culture assay (TCI phenotype) and hybridization to the probes described below without prior knowledge of their serotype or source to ensure an unbiased evaluation. *E. coli* strain HB101 (FhsdS20 ($r_B$-,$m_B$-) recA13 ara14 proA2 lacY1 qalK2 rpsL20 xY15 mt11) (Bachman, *Bacteriol. Rev.* (1972) 36:525–557) carrying the recombinant plasmids pRI203, pVM101, or pVM103 were maintained on LB agar plates containing 50 μg/ml ampicillin (Ap). Human laryngeal epithelial (HEp-2) cells were maintained and prepared for the invasion assay as previously described (Finlay and Falkow, (1987) supra). Yersinia strains were grown at 28° C. with aeration for 12 to 18 hours in LB for the invasion assays.

Nucleic Acid Purification and Probe Preparation

Chromosomal DNA was isolated as described (Mekalanos, Cell (1983) 35:253–263). Plasmid DNA was purified by a cleared lysate method followed by CsCl equilibrium density centrifugation as described (Maniatis et al., (1982) supra). DNA restriction enzymes were purchased from Bethesda Research Laboratory, and were used according to the instructions of the manufacturer. DNA probes were prepared as follows. Plasmid DNA was digested with the appropriate restriction endonucleases, and the fragments were separated by electrophoresis through a 0.7% agarose gel. The DNA fragments were purified from the agarose gel slices using Geneclean (Bio101, La Jolla, Calif.). The purified fragments were then labelled with $^{32}p$ by nick translation for use as probes as previously described (Maniatis et al., *Proc. Natl. Acad. Sci. USA* (1975) 72:1184–1188).

Southern Hybridization Analysis

Chromosomal DNA was digested to completion with EcoRV, and the fragments were separated by electrophoresis through a 0.7% agarose gel. The separated DNA fragments were transferred to nitrocellulose (Schleicher & Schuell, Keens, NH) as described by Southern. Hybridizations were performed at either medium or low stringency. Medium stringency conditions were as follows: the filter is prehybridized for 1 hour at 37° C. in 35% formamide/4x SSC/0.1% SDS/1mM EDTA/1X Denhardts. The prehybridization solution is then removed and hybridization solution (same as prehybridization solution) containing 250 μg/ml calf thymus DNA and the boiled probe is added to the filter. After hybridization for 12 to 18 hours at 37° C. the filter was washed three times with 5x SSC/0.1% SDS at 65° C. for 15 minutes, 10 minutes, and 5 minutes. Then the filter was washed in 2x SSC at room temperature for minutes, air dried, and exposed to Kodak XAR-5 film. Low stringency conditions are the same as medium stringency except that 20% formamide is used in the prehybridization and hybridization solutions. The filters can be reused if washed in 0.25 M NaOH at room temperature for 6 to 10 hours, and rinsed briefly in 2x SSC. Probe results presented for a given strain were obtained using a single filter that was reprobed several times. This allowed direct comparison of fragments that hybridized to the various probes used.

Colony blots were hybridized as above. Individual colony blots were used for each probe rather than rehybridizing the same filter.

Tissue Culture Invasion Assay (TCI)

Either quantitative or qualitative TCI assays were performed. The quantitative assay is as follows: bacteria (approximately $2 \times 10^7$) were added to each well of a 24 well microtiter plate which had been seeded with tissue culture cells the previous day as described (Finlay and Falkow, (1987) supra). The microtiter plates were centrifuged for 10 minutes/162 xg/ambient temperature, and then incubated in 5% $CO_2$ at 37° C. After 90 minutes the tissue culture medium was removed, and the cells were washed three times with phosphate buffered saline (PBS) to remove non-adherent bacteria. Fresh tissue culture medium containing 100 μg/ml gentamicin was then added, and the plates were reincubated as above. After 90 minutes the medium was removed, and the monolayers were washed twice with PBS to remove the gentamicin. The tissue culture cells were then lysed to release intracellular bacteria with 0.2 ml of 1% Triton X-100. After five minutes, 0.8 ml of LB was added bringing the final concentration of Triton X-100 to 0.2%- The suspension was then diluted and plated on the appropriate bacteriological medium to determine viable counts. Viable counts of the initial bacterial culture were also determined. Results are expressed as follows:

$$\text{invasion} = 100 \times (\text{\#bacteria resistant to gentamicin}/\text{\#bacteria added})$$

The qualitative assay was performed as described above. After washing twice with PBS to remove the gentamicin, the tissue culture cells were lysed to release intracellular bacteria by adding 0.2 ml of 1% Triton X-100 to each well. After five minutes, 0.8 ml of LB was added. Fifty microliters of this suspension was then spread on an LB agar plate. Results are scored as either TCI+ or TCI−. TCI+ strains give almost confluent growth on the LB plate after the assay, whereas TCI− strains give a few isolated colonies.

RESULTS

TCI Phenotype

One hundred seventy-seven Yersinia strains were examined for their TCI phenotype (1 *Y. pestis*, 10 *T. pseudotuberculosis* 149 *Y. enterocolitica*, 4 *Y. frederiksenii*, 4 *Y. kristensenii*, 3 *Y. intermedia*, 2 *Y. aldovae*, 4 new species 9). These strains were isolated in a variety of geographical locales and over a time span of more than ten years; nine of the *Y. enterocolitica* strains were isolated from four outbreaks and thus probably represent only four distinct isolates. Twenty-six different serotypes are represented. Forty strains were examined quantitatively and qualitatively. Values for TCI+ strains using the quantitative assay ranged from 0.6% to 7.8%; values for TCI− strains ranged from 0.014% to 0.023%. In all cases there was at least a 26-fold difference between the TCI+ and TCI− strains. Thereafter the qualitative TCI assay was used. No strain gave ambiguous results; even strains that exhibited extensive cytotoxic activity were still clearly invasive. The results observed indicate that serotypes that are commonly found in the clinical setting were TCI+, whereas serotypes commonly isolated from the environment were TCI−. This result is in agreement with previous studies that have observed a good correlation between potential pathogenicity, as defined by serotype, and the ability to invade tissue culture cells (Lee et al., *Can. J. Microbiol.* (1977) 23:1714–1722; Schieman and Denenish, *Infect. Immun.* (1982) 35:497–506).

Probes

Four different probes were used in the experiments. The Inv-Ent probe was a 3.6 kb ClaI fragment purified from pVM101. This probe contained most of the inv gene from *Y. enterocolitica* in addition to adjacent sequences; it is known that DNA to the left of the EcoRV site is not required for inv activity. The Inv-Pstb probe was a 2.4 kb ClaI-XhoI fragment purified from pRI203 (Isberg et al., *Cell* (1987) 50:769–778). This fragment contained only sequences internal to the *Y. pseudotuberculosis* inv gene. Although Southern blot analysis indicated *Y. enterocolitica* and *Y. pseudotuberculosis* inv genes were homologous, no similarity was observed in their restriction maps. Both these inv genes promote a high level of invasion by *E. coli* HB101 of a variety of tissue culture cell lines.

Two probes were used from the *Y. enterocolitica* ail locus, AIL-B and AIL-C. AIL-B was a 900 bp AvaI-ClaI fragment from pVM103. AIL-C was a 1.2 kb ClaI-AvaI fragment from pVM103. Genetic analysis with the transposon Tn5 had indicated that DNA contained within the AIL-C probe was required for the AIl phenotype. No Tn5 insertions eliminating the AIl phenotype have been isolated in AIL-B. Preliminary DNA sequence data suggests that only six base pairs of the ail coding sequence are located within AIL-B; the remainder of the ail coding sequence is contained within AIL-C.

Most blots were also probed with labelled pBR322 (the cloning vector). Although some strains clearly had homology to pBR322, the hybridizing fragments were different from those hybridizing to the inv or ail probes.

Location of inv and ail

The inv and ail genes were cloned from *Y. enterocolitica* strain 8081c. Strain 8081c lacks detectable plasmid DNA and plasmid associated phenotypes, but it is possible that the plasmid has integrated into the chromosome. To determine if inv and ail are truly chromosomal genes rather than plasmid genes Southern analysis was performed of purified virulence plasmid DNA and chromosomal DNA from strain 8081c. None of the probes hybridized to the plasmid DNA indicating that the inv and ail genes are not located on the plasmid. The restriction endonuclease used to digest the DNA (EcoRV) cuts once within the Inv-Ent probe so two fragments from chromosomal DNA were found that hybridized to the Inv-Ent probe. The AIL-C probe hybridized to a single fragment from chromosomal DNA, but the AIL-B probe hybridized to several chromosomal DNA fragments. The restriction endonuclease used (EcoRV) does not cut within the AIL-B probe, therefore a sequence present within AIL-B is repeated within the chromosome. Although there are indications that the virulence plasmid may contain a repeated sequence, it appears to be distinct from the repeated sequence identified by the AIL-B probe. The results also indicate that inv and ail are probably single copy loci and, because probes derived from these genes hybridize to different fragments, are not adjacent to each other on the chromosome.

Hybridization of AIL-C to DNA from *Y. enterocolitica* Strains

Many non-pathogenic strains of *Y. enterocolitica* were TCI−. We supposed they might be missing essential genes required for invasion, or they might contain the appropriate gene in a nonfunctional form. To investigate if these possibilities pertained to ail or inv we did either Southern or colony blot analysis of the 149 *Y. enterocolitica* strains. The AIL-C probe did not hybridize to DNA from all strains. If one compares hybridization to AIL-C and the TCI phenotype one finds that 85 of 86 TCI+ strains had homology to AIL-C, whereas only 1 of 63 TCI− strains had homology to AIL-C. Thus there was a better than 98% correlation between the AIL-C and TCI phenotypes. This result supports the hypothesis that the ail locus encodes a virulence factor(s).

Hybridization to AIL-B to DNA from *Y. enterocolitica* Strains

The AIL-B probe like the AIL-C probe did not usually hybridize to TCI− strains. However, the TCI+ strains can be divided into two distinct groups —those that showed strong hybridization to AIL-B, and those that showed weak or no hybridization to AIL-B. Strains which hybridized strongly to AIL-B always had multiple fragments that hybridized; the number and size of these fragments varied from strain to strain. Strains which hybridized only weakly to AIL-B always had only one fragment that hybridized. This fragment was usually identical to the fragment that hybridized to AIL-C. Preliminary sequencing results indicate that the ail coding region extends only 6 bp into AIL-B. This suggests that the weak hybridization seen to AIL-B in these strains could be due to a short sequence associated with ail, but that these strains lack sequences present in AIL-B that are repeated in the chromosome of strains that hybridize strongly to this probe.

TCI+ strains that hybridized strongly to AIL-B include the serotypes 013a,13b; 018; 020; 021; 04; 04,32; 04,33; and 08. TCI+strains that hybridize weakly or not at all to AIL-B include the serotypes 01,2,3; 03; 05,27; and 09. Interestingly this represents a clean division between the pathogenic "American" serotypes (i.e., those isolated only in North America), and other pathogenic serotypes isolated in Europe, Japan, Southern Africa, and Canada with regard to AIL-B phenotype. Although both groups of potentially pathogenic serotypes have the ail gene, the non-"American" strains appear to lack a sequence located near ail that is found repeated in the chromosome of "American" strains.

Hybridization of Inv-Ent and Inv-Pstb to DNA from Y. enterocolitica Strains

The Inv-Ent probe hybridized to DNA isolated from all strains, nevertheless there were differences between pathogenic and non-pathogenic strains. We observed several distinct hybridization patterns. We have labelled them type I, II, I/II, III, IV, and V. Type I strains had 9.5 kb and 4.0 kb fragments, and type II had 9.7 kb and 3.8 kb fragments, that hybridized to the Inv-Ent probe. There were 36 strains that were type I, of these 34 were TCI+. Type I/II shared a 9.7 kb fragment with Type II and a 4.0 kb fragment with type I; all six type I/II strains were TCI+. The remaining four groups, II, III, IV, and V were all TCI−. Type V shared a 9.5 kb fragment with type I and in addition had a 5.0 kb fragment that hybridizes to Inv-Ent. The hybridization of Inv-Ent to type III was weak relative to the hybridization observed with other strains. The type III pattern appears identical to the hybridization pattern observed for Y. intermedia. Type IV is a catch-all for strains with unique hybridization patterns. Overall there was a correlation between strains that are TCI+ and the type I or I/II hybridization pattern, while strains that were TCI− exhibit type II, III, IV, or V hybridization patterns.

Unlike the Inv-Ent probe, the Inv-Pstb probe contained only inv coding sequence. Therefore fragments that hybridized to Inv-Pstb were those with sequences related to the inv gene itself. The Inv-Pstb probe hybridized to all Y. enterocolitica strains tested except for the type III strains. In each case the fragment that hybridizes to Inv-Pstb is identical to one of the fragments recognized by Inv-Ent. InvPstb hybridized to the 9.5 kb fragment of types I and V, and to the 9.7 kb fragment of types II and I/II. This result indicates that the hybridization of Inv-Ent to these fragments probably represents homology to inv sequences. Hybridization of Inv-Ent to other fragments is probably due to homology to DNA sequences adjacent to inv. The results using the Inv-Pstb probe also suggest that type III strains do not have an inv gene and that the hybridization observed with the Inv-Ent probe is due to sequences adjacent to inv. Alternatively, but less likely, the type III strains have diverged more from the Y. pseudotuberculosis inv gene than have other Y. enterocolitica strains. As mentioned above the type III hybridization pattern is like that seen for Y. intermedia strains, so it is possible that these strains have been incorrectly speciated.

Hybridization Phenotypes of Strains Isolated During Several Outbreaks

As noted above, there is an extremely good correlation between the ability to invade tissue culture cells and hybridization to the inv and ail probes. Is a similar correlation seen between Y. enterocolitica strains that clearly caused clinical disease and hybridization to the probes? To address this question we examined strains previously characterized from outbreaks of yersiniosis. The strains examined included those isolated from patients and those isolated from asymptomatic individuals at the same time in the see region. The data indicate that all Y. enterocolitica isolates that are strongly implicated as the cause of disease were TCI+, whereas strains isolated from asymptomatic individuals were either TCI− or TCI+. As were other TCI+strains, these strains were type I with the Inv-Ent probe. A strain isolated from an asymptomatic fatally member of a patient was TCI− and was type II with the Inv-Ent probe.

The strains isolated from patients are AIL-C+ and AIL-B+. The TCI− strains were AIL-B− and AIL-C− as was previously observed for other TCI− strains. The pattern of hybridization of AIL-B to DNA from random Y. enterocolitica isolates varied from strain to strain. However, strains isolated from the same outbreak exhibited identical hybridization patterns to the AIL-B probe. This probe may, therefore, serve as a useful marker for identifying the source, and following a particular epidemic.

Presence of inv and all Sequences Among the Yersiniae

Three species of Yersinia are generally recognized as pathogenic for animals: Y. pestis, Y-pseudotuberculosis, Y. enterocolitica. Several other Yersinia species have been defined, but these are generally considered to be non-pathogenic. Are the differences observed, using the inv and ail probes, between pathogenic and non-pathogenic Y. enterocolitica also true for the genus Yersinia as a whole? DNA isolated from all species of Yersinia tested exhibited homology to the Inv-Ent probe, but only the pathogenic species showed strong homology to the Inv-Pstb probe. The DNA fragments hybridizing to Inv-Pstb and Inv-Ent for Y. pestis, Y. pseudotuberculosis, and Y. enterocolitica were the same, suggesting these fragments encode the inv gene. In contrast, Y. aldovae, Y. intermedia, Y. frederiksenii, Y. kristensenii, and new species 9 showed only very weak hybridization to Inv-Pstb, and the fragments hybridizing to Inv-Pstb were not the same as those hybridizing to Inv-Ent, suggesting the hybridization to Inv-Ent may be due to sequences present in the probe adjacent to inv rather than to inv itself.

The AIL-B and AIL-C probes both hybridized to DNA isolated from Y. pestis, and Y. pseudotuberculosis as well as to pathogenic Y. enterocolitica. The fragments that hybridized to these two probes differed though, indicating either that the AIL-B and AIL-C sequences are separated on the chromosome of these species (unlike Y. enterocolitica), or that an EcoRV site separates these sequences. The AIL-B probe I hybridized strongly to only one DNA fragment in Y. pestis and Y. pseudotuberculosis strain YPIII, but after longer exposure several additional weak hybridization signals could be observed for Y. pestis. DNA isolated from twenty-three different species in addition to the Yersinia spp.

was also examined for hybridization to these probes using low stringency conditions. No hybridization to the Inv-Ent probe was observed, suggesting this probe contains Yersinia specific sequences. No hybridization to the AIL-C probe was observed either, suggesting this probe contains DNA sequences specific to pathogenic Yersiniae. Only DNA isolated from a strain of *Klebsiella pneumonia* hybridized to AIL-B; four hybridizing fragments were observed when digested with the restriction endonuclease EcoRV, suggesting the sequence is repeated in *Klebsiella pneumonia* as it is in *Y. enterocolitica*.

Hybridization of inv and ail to *Y. pseudotuberculosis*

As noted above, all four probes used in this study hybridized to DNA isolated from *Y. pseudotuberculosis* strain YPIII. To determine if this is generally true we examined nine other *Y. pseudotuberculosis* strains isolated from both humans and animals. All of these strains were TCI+ and hybridized to all probes. Two different hybridization patterns were observed with the Inv-Pstb probe, but there was no obvious correlation between serotype or source, and hybridization pattern. In addition to the fragment that hybridized to AIL-B in all strains, a few strains also show four other weakly hybridizing fragments; these fragments are the same for all strains that exhibit the phenotype. Although only a few *Y. pseudotuberculosis* strains were examined it appears that the species *Y. pseudotuberculosis* is more homogenous with regard to the in$_v$ and ail loci than is *Y. enterocolitica*.

The above results demonstrate that tissue culture invasiveness is a good indicator of potential pathogenicity. This has been proposed in several other studies. Lee, *Contr. Microbiol. Immunol.* (1979) 5:228–233; Lee et al., *Can. J. Microbiol.* (1977) 23:17141722; Schiman and Devenish, *Infect. Immun.* (1982) 35:497–506; and Une, *Microbiol. Immunol.* (1977) 21,365–377. Strains strongly implicated as the cause of outbreaks of gastrointestinal disease are exclusively TCI+, and strains isolated from healthy individuals at the same time and locale as strains associated with disease are often TCI−. These results support the hypothesis that tissue invasiveness is an important aspect of Yersinia pathogenesis and that the ability to invade tissue culture cells is a good in vitro assay for the invasive ability of virulent strains.

The following describes the identification of the ail gene analog in *S. typhimurium*.

MATERIALS AND METHODS

Strains and Media. All rich media was Luria broth (LB) and all minimal media was M9 (Davis, et al., (1980) *Advanced Bacterial Genetics*, Cold Spring Harbor Lab, Cold Spring Harbor, NY p.21). The construction of *S. typhimurium* strain CS119 pagCl::TnphoA phoN2 zxx::6251 Tn10d-Cam was previously described (Fields, et al., (1989) *Science* 243:1059–1062) American Type Culture Collection (ATTC) *S. typhimurium* strain 10428 was the wild type parent of CC119. Other strains derived from ATCC 10428 included CS018 which is isogenic to CS119 except for phoP105::Tn10d CS022, phoP-24 (Con) (Miller and Mekalanos (1989) *J. Bacteriol*; Fields, et al., (1989) supra), and CS015 phoP102::Tn10d-Cam. Other wild type strains used for preparation of chromosomal DNA included *S. typhimuriuan* LT2 (ATCC 15277), *S. typhimurium* Q1 and *S. drypool* (Dr. J. Peterson U. Texas Medical Branch, Galveston), and *Salmonella typhi* Ty2 (Dr. Caroline Hardegree, Food and Drug Administration). AP activity was screened on solid media using the chromogenic phosphatase substrate 5-bromo-4-chloro-3-indolyl phosphate, (XP). AP assays were performed as previously described and are reported in units as defined by Miller ((1972) Experiments in Molecular Genetics, Cold Spring Harbor Lab, Cold Spring Harbor, N.Y. pp. 352–355.

Protein electrophoresis and Western blot analysis. One dimensional protein gel electrophoresis was performed by the method of Laemmli and blot hybridization using antibody to AP was performed as previously described (Peterson and Mekalanos (1988) *Infect. Immun.* 56:2822–2829). Whole cell protein extracts were prepared from saturated cultures grown in LB at 37° C. with aeration, by boiling the cells in SDS-PAGE sample buffer (Laemmli (1970) *Nature* 227,680–685). Two dimensional gel electrophoresis was performed by the method of O'Farrell. Proteins in the 10% polyacrylamide slab gels were visualized by silver staining (Meril et al., (1984) *Meth. in Enzymology* 104:441)

DNA analysis and sequencing. Chromosomal DNA was prepared by the method of Mekalanos ((1983) *Cell* 35:253–263). DNA, size fractionated in agarose gels, was transferred to nitrocellulose (for blot hybridization) by the method of Southern ((1975) *J. Mol. Biol.* 98:503–517). DNA probes for Southern hybridization analysis were radiolabeled by the random primer method (Feinberg and Vogelstein (1984) *Anal. Biochem.*) Plasmid DNA was transformed into *E. coli* and Salmonella by calcium chloride and heat shock (Machlachlan and Sanderson (1985) *J. Bacteriol.* 161:442–445), or by electroporation using a Genepulser apparatus (Biorad) as recommended by the manufacturer (Domer et al., (1988) *Nucl. Acids Res.* 16:6127–6145). DNA sequencing was performed by the dideoxy chain termination method of Sanger as modified for use with Sequenase (U.S. Biochemical). Oligonucleotides were synthesized on an Applied Biosystems machine and used as primers for sequencing reactions. Specific primers unique to the two ends of Tn pboA, one of which corresponds to the alkaline phosphatase coding sequence and the other to the right IS50 sequence were used to sequence the Junctions of the transposon insertion.

RNA purification and analysis. RNA was purified from early log phase Salmonella cultures by the hot phenol method (Case et al., *Gene* 72:219–236), and run in agarose-formaldehyde gels for blot hybridization analysis (Thomas (1980) *PNAS USA* 77:5201).

RESULTS

Identification of an 18 kDa protein missing in a PagC mutant of *S. typhimurium*. Strain CS119 was analyzed by two dimensional protein electrophoresis to detect protein species that might be absent as a result of the TnphoA insertion. Identification of multiple changes in the protein profile of CS119 relative to the parent strain supports that the expression of a large operon or a regulatory locus was altered as a result of the transposon insertion. Only a single change in protein species was observed when strains, isogenic except for their transposon insertions, were subjected to this analysis. A single protein of approximately 18 kilodaltons (kDa) and pI of approximately 8.0 is missing in the strain with the pagC::TnphoA insertion. This 18 kDa species is also missing in Salmonella strains with mutations in phoP and phoQ. The size and pI of this protein was similar to that predicted to be disrupted by insertion of TnphoA into pagC.

Analysis of the PagC-AP fusion protein. Western blot analysis using antibody to AP was performed to determine the size of the AP fusion protein produced by strain CS119 and to determine the Mount of *S. typhimurium* DNA sequence needed to encode the fusion protein. The PagC-AP fusion protein is similar in size to native alkaline phosphatase at 45 kDa, indicating that either a small coding sequence of Salmonella DNA is contributing to the gene fusion, or a large unstable fusion is produced. The lack of production of the 45 kDa PagC-AP fusion protein in strain CS018, isogenic to strain CS119 except for a phoP::Tn10d insertion, further demonstrates the dependence on an intact phoP locus for efficient expression of pagC.

Cloning of the pagC::TnphoA insertion. Chromosomal DNA was prepared from *S. typhimurium* strain CS119 and Southern hybridization analysis was performed using a gene fragment from TnphoA as a probe. This fragment hybridizes preferentially to one end of TnphoA if the restriction enzyme BamHI is used in the analysis (Peterson and Mekalanos (1988) supra). Therefore, a number of double restriction endonuclease digestions including BamH1 were used to determine a rough physical map of the restriction endonuclease sites in the region of the pagC::TnphoA fusion. This analysis indicated that digestion with the restriction endonucleases XbaI and EcoRV yielded a single DNA fragment that included the pagC::TnphoA insertion in addition to several kilobases of flanking DNA. Therefore, chromosomal DNA from strain CS119 was digested with XbaI and EcoRV and ligated into the bacterial plasmid vector pUC19 that had been digested with the restriction endonucleases XbaI and SmaI. This DNA was electroporated into the *E. coli* strain DHS-alpha and colonies were plated onto LB agar containing the antibiotics kanamycin (TnphoA encoded) and ampicillin (pUC19 encoded). A single epicillin and kanamycin resistant clone containing a plasmid designated pSM100 was selected for further study.

A radiolabeled DNA probe from pSM100 was constructed and used in Southern hybridization analysis of strain CS119 and its wild type parent ATCC 10428 to prove that we had cloned the pagC::TnphoA fusion. The probe contained sequences immediately adjacent to the transposon at the opposite end of the alkaline phosphatase gene (HpaI endonuclease generated DNA fragment that included 186 bases of the right IS50 of the transposon and 1278 bases of Salmonella DNA corresponding to the region between 161 and 1439). As expected, the DNA fragment from the strain containing the transposon insertion, CS119, was approximately 7.7 kb (size of TnphoA) larger in size than the fragment from the wild type strain that hybridizes to the probe. This was consistent with the supposition that we have cloned the pagC::TnphoA fusion. In addition, a derivative of plasmid pSM100, pSM101 (which did not allow expression of the pagC-phoA gene fusion off the lac promoter), was transformed into phoP− (strain CS015) and phoN− (strain CS019) Salmonella strains and the cloned AP activity was found to be dependent on phoP for expression. Therefore we concluded that the cloned DNA contained the pagC::TnphoA fusion.

Mapping of restriction endonuclease sites- DNA sequencing and determination of the pagC gene product Restriction endonuclease analysis of plasmid pSM100 was performed to obtain a physical map of the pagC locus, and to determine the direction of transcription. Appropriate DNA subclones were generated and sequence was obtained from the junctions of the transposon and Salmonella DNA. The sequence was also obtained for Salmonella DNA extending from the PstI site immediately upstream of the fusion to the EcoRI site downstream of the fusion. The correct reading frame of the DNA sequence was deduced from that required to synthesize an active AP gene fusion. The deduced amino acid sequence contains a methionine start codon 33 amino acids from the fusion of PagC and AP. This 33 amino acid pagC contribution to the fusion protein was consistent with that observed in Western blot analysis and contains a hydrophobic N-terminal region, identified by the method of Kyle and Doolittle ( ( 1892 ) *J. Mol. Biol.* 157: 105–132), that is a typical bacterial signal sequence (Yon Heinje (1985) *J. Mol. Biol.* 184:99–105). Specifically, amino acid 2 is a positively charged lysine, followed by a hydrophobic domain and amino acid 24 is a negatively charged aspartate residue. A consensus cleavage site for this leader peptide is predicted to be at an alanins residue at amino acid 23 (von Heinje (1984) *J. Mol. Biol.* 173:243–251). The DNA sequence also revealed a typical ribosomal binding site at 6–12 nucleotides 5' to the predicted start of translation. This suggested that the open reading frame was, in fact, translated and further supported the assumption that this was the deduced amino acid sequence of the PagC protein interrupted by the TnphoA insertion. The deduced amino acid sequence of the open reading frame was predicted to encode a 188 amino acid protein with a predicted pi=8.2. This was consistent with the 18 kDa protein of pI-8.0, noted to be absent in the 2-D polyacrylamide gel analysis of strain CS119. Therefore identification of the pagC gene product appears established. As documented below, the pagC transcript is approximately 900 nucleotides in length. This is approximately 300 nucleotides greater than that which is devoted to pagC coding sequence, and would seem to preclude the pagC transcript encoding another protein greater than 100 amino acids in size. Therefore, the identified pagC gene product is likely to be the protein essential to virulence and macrophage survival. The pagC gene may be part of a larger operon, but if that is the case, it appears to be the last gene of the operon, and the upstream gene would encode a small protein.

The pagC gene is present in other strains of Salmonella. To test whether other *S. typhimurium* strains LT2, and Q1, as well as *S. typhi* and *S. drypool* contained the pagC gene, chromosomal DNA was prepared from these strains and screened by blot hybridization analysis using a pagC gene probe. All Salmonella strains examined demonstrated similar strong hybridization to an 8.0 kb EcoRV-KpnI and a 4.0 kb AccI restriction endonuclease fragment suggesting that pagC is a virulence gene common to Salmonella species.

Identification of the pagC encoded RNA. We purified and analyzed RNA from *S. typhimurium* strains ATCC 10428 (wild type), CS015 phoP 102::Tn10d-Cam, and C5022 pho-24 (Con) to determine the size of the pagC transcript as well as its dependence on phoP for transcription. An approximately 900 nucleotide RNA is encoded by pagC and this RNA is clearly highly expressed in a strain with a constitutive phenotype of pag activation as compared to wild type and phoP− bacteria. This suggests, as expected by gene fusion analysis, that pagC is transcriptionally regulated by the phoP gene product and not expressed in early log phase cultures grown in rich media.

Similarity of PagC to Ail and Lom. A computer analysis of protein similarity using the National Biomedical Research Foundation/Protein Identification Resource (George et al., (1986) Nucl. Acids. Res. 14:11-15) protein sequence base was conducted to identify other proteins that had similarity to PagC in an attempt to find clues to the molecular function of this protein. Remarkably, PagC was found to be similar to a bacteriophage lambda protein, Lom that has been localized to the outer membrane in minicell analysis (Reeve and Shaw (1979) Mol. Gen. Genetics 172:243) as well as demonstrated to be expressed by lambda lysogene of E. coli. The deduced amino acid sequence of the cloned ail gene product of Y. enterocolitica was determined and found to also be similar to Lom. Therefore, we performed a protein family sequence alignment using a computer algorithm and searched for other members of the family in the data base using a method that has been shown to be more diagnostic for family membership than searching individual sequences (Smith and Smith (1990) PNAS USA 87, 118-122) However, no other similarities were found. Regions of similarity are located not only in the leader peptide and transmembrane domains but throughout the protein.

Invasion phenotype of wild type pagC Salmonella strains. Because of the strong similarity of PagC to ail, PagC— and PhoP— strains were examined in tissue culture models of invasion to assess whether the PagC protein functions as an invasion factor as well as a macrophage survival protein.

TABLE 6

Invasive phenotype of wild type S. typhimurium strain ATCC 10428 and pagC and phoP mutants[a]

| Bacterial Strain | HEp-2 | CHO | % Invasion MDCK |
|---|---|---|---|
| ATCC 10428 (wild type) | 6.35 | 6.55 | 8.55 |
| CS119 (pagC::Tn phoA | 4.73 | 4.90 | 6.68 |
| CS015 (phoP-) | 1.87 | 2.34 | 4.46 |
| CS022 (phoP constitutive) | 1.82 | 3.18 | 3.75 |

[a]Salmonella typhimurium strains were grown at 28° C. with aeration for 12 to 18 h in LB for the invasion assay. Bacteria ($2/10^7$) were added to each well of a 24-well microdilution dish which had been seeded with the indicated tissue culture cells the previous day. The invasion assay was performed as previously described (Miller and Falkow (1988) Infect. Immun. 56:1242-1248) with the exception that the microtiter plates were not centrifuged prior to the first incubation. Values are the averages of duplicate samples, and reflect similar results from several experiments.

We were enable to detect more than a modest defect in these strains in these assays. Therefore, we conclude that the PagC protein may not function as an invasion protein, or is not the only pathway by which Salmonella invades epithelial cells. This is consistent with the fact that orally administered phoP— Salmonella strains pass efficiently from the gut to the liver and spleen.

The above results demonstrate that a number of invasive organisms have one or more common invasive gene(s) which are homologous in a plurality of species. That the gene, inv, as well as a second gene, ail, may be readily transferred to a non-invasive microorganism host to provide for invasion by such microorganism into mammalian cells. Furthermore, DNA from the genes may be used for an in vitro assay for determining pathogenicity of Yersinia species, as well as other species. The invasive genes find further use in identifying strains, evaluating levels of pathogenicity and relationships between pathogenicity and invasion genes.

The mammalian cells are able to endocytose the entire microbial cell based on the presence of a particular structure encoded on the surface membrane of the microorganism. The invasive phenotype can be used for diverse purposes, such as the introduction of exogenous DNA or other molecules into a mammalian host, induction of an immune response to one or a plurality of antigene associated with pathogene, so as to be useful as vaccines, for production of antiserum having a spectrum of antibodies to a spectrum of pathogene, and for the production of proteins which may be used to inhibit invasion of pathogene in mammalian host cells.

Studies on the Effects of Growth Conditions on the Adherence and Invasiveness of Salmonella Bacterial Strains and Growth Conditions Salmonella choleraesuis strain SL2824 (Nnalue, N. A. & Stocker, B. A.D. (1986) Infect. Immun. 54, 635-640) and Salmonella typhi strain 404Tywere obtained from B.A.D. Stocker (Stanford University School of Medicine, CA). 404Ty is a aaroA148 derivative of an Indonesian strain 3083/30 originally characterized by L. LeMinor (Institut Pasteur, Paris, France) which has two flagellar antigen phases, d and z66 (Guinee, P. A. M., Jansen, W. H., Mass, H. M. E., LeMinor, L. & Beaud, R. (1981) Ann. Microbiol. (Inst. Pasteur) 132A, 331-334). Salmonella typhimuirum strains TN1909 and TN1910, obtained from Charles Miller (Case Western Reserve University, Ohio), are isogenic strains containing the oxrA+ and oxrA1 loci, respectively. S. typhimurium strain LT2 (DB21)) was obtained from David Botstein (Genentech, CA). Salmonella were grown in LB broth and on LB agar media 9GIBCO, Grand Island, N.Y.), alone or supplemented with 2,3-dihydroxybenzoic acid (DBH) (10 $\mu$g/ml) (Sigma, St. Louis, Mo.) which is required for optimal growth of the xaroA mutant strain.

Cultures used in some experiments (Table 7 and Table 8, Expt. III) were grown in LB broth containing antifoam (Sigma Chemical Co., St. Louis, Mo.). The presence of antifoam does not affect the induction or assay of bacterial invasiveness (data not shown). Initially, a culture was grown to logarithmic phase in LB broth containing antifoam while bubbled with air from the laboratory air lines for 2½ hours. This culture was diluted to prepare three cultures which were gently bubbled with different gas mixtures, 5% $CO_2$/95% $N_2$, 1% $O_2$/5% $CO_2$/94% $N_2$ or 20% $O_2$/5% $CO_2$/75% $N_2$ (Liquid Carbonic Specialty Gas Corp., San Carlos, CA). After 3 hours of additional growth, the final culture density of each culture was $-4 \times 10^8$ CFU/ml (colony-forming units per ml) (Table 7, Expt I) and $-2 \times 10^8$. CFU/ml (Table 7, Expt. II).

Non-agitated cultures were prepared by inoculation of 2 ml of LB broth in $16 \times 150$ mm borosilicate tubes with 0.04 ml of a stationary phase culture. For determining invasiveness, as a percent of inoculum surviving gentamicin, separate cultures were prepared to allow uninterrupted incubation of each sample. It was characteristic of such cultures that, during the initial 3 hour incubation at 37° C., the culture density increased from $10^8$ CFU/ml to $4 \times 10^8$ CFU/ml. Bacterial growth was much slower during the next 4 hours; the culture density after 7 hours of growth was only $7 \times 10^8$CFU/ml. We considered that bacteria from such cultures were in the late logarithmic phase of growth.

Agitated cultures were prepared by inoculation of 1 or 2 ml of LB broth in $16 \times 150$ nun borosilicate tubes with a stationary phase culture (a 1:1,000 or 1:50 dilution factor) and placing the tubes on a roller drum (New Brunswick Scientific, Edison, N.J., 80rpm) at 37° C. Under these growth conditions, logarithmically growing cultures had $\leq 10^9$ CFU ml. For the experiment concerned with a time course of invasiveness, separate cultures were prepared to allow uninterrupted incubation of each sample.

Overnight cultures were prepared as a source of bacteria in stationary phase by inoculation of 2 ml of broth with $<10^6$ CFU and growth with agitation, except for that used for the experiment determining entry of bacteria S. choleraesuis of MDCK cells. In this case, a culture was grown overnight without agitation from a heavy inoculum, as previously described (Finlay, B. B. & Falkow, S. (1988) Biochimie 70: 1089–1099). Results were similar to those obtained when stationary phase bacteria from an agitated culture were used instead.

Strains were grown at 37° C. with the exception of strains TN1909 and TN1910 which carry a temperature-sensitive Mu dl prophage; they were grown at 30° C. CFU were determined by plating serial dilutions onto LB agar medium.

MDCK cells and growth conditions.

Strain 1 MDCK cells (Gumbiner, B & Simons, K (1986) J. Cell Biol. 102: 457–468.) were grown in MEM Eagle medium with Earle's salts (Cellgro/Mediatech, Washington, D.C.), 5% fetal bovine serum (GIBCO, Grand Island, N.Y.), without antibiotics. Monolayers for adherence and invasion assays were prepared by seeding approximately $10^5$ cells into each well of a 24-multiwell tissue culture plate and incubating overnight. MDCK cells between passage 40 and 60 were used for all assays except for those in Table 7 and Table 8 (Expt. III) when cells between passage and 10 were used. The absolute values for bacterial adherence and invasion were tenfold lower when MDCK cells between passage 8 and 10 were used vs. when those between passage 40 and 60 were used. It is possible that a property of the MDCK cells changed after many serial subcultures resulting in an increased efficiency of bacterial adherence and invasion. The conclusions of this study appear to be unaffected by this potential change in MDCK cells.

Adherence assay

The medium overlying the MDCK monolayers was replaced with 1 ml of ice-cold tissue culture medium and the multi-well dish was placed in an ice-water bath for 30 minutes prior to the assay. Bacterial samples were diluted if necessary in LB broth to approximately $10^8$ to $4 \times 10^8$ CFU/ml so that addition of 40 $\mu$l of each bacterial sample to the MDCK monolayers represented an initial inoculum of $5 \times 10^6$ to $2 \times 10^7$ CFU. Control wells without mammalian cells were similarly prepared to quantitate non-specific bacterial adherence to plastic. The bacteria were allowed to adhere on ice for 60 minutes and then each well was rinsed five times with 1–2 ml of ice-cold phosphate-buffered saline (PBS). Adherent bacteria were released by incubation with 0.2 ml 0.1% Triton X-100 (Sigma Chemical Co., St. Louis, Mo.) for 5–10 minutes. 0.8 ml LB broth was then added and each sample was vigorously mixed using a pasteur pipet. Adherent bacteria were quantitated by plating for CFU on LB agar media.

In order to measure internalization of adherent bacteria, bacteria were allowed to adhere as described above. After removal of non-adherent bacteria with the PBS washes, 1 ml of pre-warmed tissue culture medium was added to each assay well and internalization of bacteria was allowed to proceed for 60 minutes at 37° C. in a 5% $CO_2$ incubator. Intracellular bacteria were quantitated after incubation with gentamicin as described below.

Invasion assay

Prior to all invasion assays, the medium overlying each MDCK monolayer was replaced with 1 ml of pre-warmed tissue culture medium. Bacterial samples were then added as described above. Invasion assays were incubated at 37° C. in a %5 $CO_2$ incubator. Assays were terminated by replacing the overlying medium with 1 ml of tissue culture medium supplemented with 100 $\mu$g/ml gentamicin. Gentamicin, an aminoglycoside antibiotic, kills extracellular bacteria while intracellular bacteria remain viable (Vaudaux, P. & Waldvogel, F. A. (1979) Antimicrob. Agents Chemother. 16: 743–749.). After incubation with the gentamicin for 120 minutes at 37° C. in a 5% $CO_2$ incubator, the cell monolayers were washed once with PBS and the viable intracellular bacteria were released by incubation with 0.2 ml 1% Triton X-100 for 5–10 minutes. Samples were vigorously mixed with 0.8 ml LB broth using a pasteur pipet. Viable bacteria were quantitated by planting for CFU on LB agar media.

For the experiment described above, initially tissue culture medium inoculated with $1.4 \times 10^7$ CFU of S. choleraesuis from a stationary phase culture was placed either on MDCK cell monolayers or in empty wells. In the first case, the entry of Salmonella into MDCK cells was measured hourly by replacing the overlying medium with tissue culture medium supplemented with 100 $\mu$g/ml gentamicin, as described above In this case, calculations were performed to determine the incremental increase in the number of bacteria that entered the MDCK cells during each one hour period. The invasiveness of the bacteria incubated in tissue culture medium alone was determined by transferring the infected medium onto MDCK cell monolayers at different times. In this case, the number of bacteria that were able to enter the cells during a one hour assay was determined, as described above.

Biosynthetic radiolabelling of Salmonella proteins

Bacterial cultures were grown at 37° C. for 5 hours to a final culture density of approximately $10^7$ CFU/ml. Cultures containing tissue culture media were grown in a 5% $CO_2$ incubator. Bacteria from 0.4 ml of each culture were washed with 1 ml of PBS and then resuspended in 80 $\mu$l M9 medium (GIBCO Laboratories, Grand Island, N.Y.) containing 0.1% glucose and 15 $\mu$Ci [$^{35}$S] methionine (Amersham Corp., Arlington Heights, Ill.). Samples were incubated at 37° C. for 1 hour and then centrifuged to harvest the bacteria. The samples were analyzed by sodium dodecyl sulfate polyacrylamide gel electrophoresis (Laemmli, U.K. (1970) Nature (London) 227,680–685.).

RESULTS

Effect of growth conditions on Salmonella invasiveness

Previous work has suggested that Salmonella is not inherently able to adhere to or enter mammalian cells (Finlay, B. B., Heffron, F. & Falkow, S. (1989) Science 243: 940–943.). Salmonella which were grown to logarithmic phase in LB broth were also found to be inherently non-adherent (Finlay, B. B., Gumbiner, B. & Falkow, S. (1989) J. Cell Biol. 107: 221–230, Finlay, B. B., Heffron, F. & Falkow, S. (1989) Science 243,:940–943.).

Experiments to measure the invasiveness of Salmonella that were grown to logarithmic and late logarithmic phase were performed. The results indicate that the invasiveness of bacteria grown under these different conditions varied dramatically. In order to understand this variation, experiments were performed so as to more carefully measure the invasiveness of bacteria during the growth of a culture. Non-agitated and agitated LB broth cultures were examined.

Non-agitated cultures of S. choleraesuis were prepared by inoculation of 2 ml of LB broth with 0.04 ml of a stationary phase culture (a 1:50 dilution factor) at $t_o$. Bacteria grown overnight to stationary phase were not able to enter MDCK cells during a one hour assay. However, after growth of bacteria in non-agitated LB broth for 3 to 7 hours, a 100-fold increase in bacterial invasiveness was observed.

Agitated cultures of S. choleraesuis were prepared by inoculating 2 ml of LB broth with a stationary phase culture (a 1:1,000 or 1:50 dilution factor) at $t_o$. When the ability of bacteria from agitated culture to enter MDCK cells was measured, dramatic differences were seen depending on the stage of growth of the bacteria sample. S. choleraesuis from cultures in logarithmic phase were not maximally invasive. However, when the culture was in late logarithmic phase, bacterial invasiveness increased at least 10-fold. The bacterial culture then lost invasiveness in stationary phase which is consistent with previous observations that bacteria grown overnight in LB broth to stationary phase are non-invasive. Similar results were also found for non-agitated and agitated cultures of S. typhi.

The dramatic differences in the invasiveness of Salmonella from different cultures were not affected by inhibition of bacterial growth and de novo protein synthesis during the assay period. Thus, in the assay performed, the difference in the ability of Salmonella to enter MDCK cells reflects an inherent property of the bacterial inoculum.

Effect of oxygen availability of Salmonella invasiveness

The above experiments show that S. choleraesuis and S. typhi from non-agitated cultures and agitated cultures in late logarithmic phase are at least 10-fold more invasive than those from agitated cultures in logarithmic phase.

A possibly significant difference between these two growth conditions that may account for the differences in Salmonella invasiveness is the availability of oxygen (Strauch, K. L., Lenk, J. B., Gamble, B. L. & Miller C. G. (1985) J. Bacteriol. 161, 673–680, Khosla, C. & Bailey, J. E. (1988) Nature 331: 633–635.).

The amount of oxygen available during bacterial growth was varied by bubbling gas mixtures containing different amounts of oxygen into the culture medium. Unlike the non-agitated and agitated cultures, these bubbled cultures ar more easily compared with one another since they can be grown with similar mixing and to similar culture densities. S. choleraesuis and S. typhimurium were grown with gases containing 0% or 1% oxygen were 6- to 70-fold more invasive than those grown with gas containing 20% oxygen (Table 7). These results confirm that Salmonella invasiveness is induced by oxygen-limited growth conditions.

TABLE 7

Effect of oxygen availability of S. choleraesuis and S. typhimurium invasiveness

| Expt. # | Bacterial species | Bacterial culture | Bacterial invasiveness(%)** |
|---|---|---|---|
| I | S. choleraesuis | non-agitated, late log | 100 ± 5 |
| | | agitated, mid-log | 8 ± 0.4 |
| | | 0% $O_2$ | 75 ± 0 |
| | | 1% $O_2$ | 62 ± 4 |
| | | 20% $O_2$ | 13 ± 3 |
| I | S. typhimurium | non-agitated, late log | 100 ± 0 |
| | | agitated, mid-log | 0.1 ± 0 |
| | | 0% $O_2$ | 41 ± 1 |
| | | 1% $O_2$ | 218 ± 18 |
| | | 20% $O_2$ | 3 ± 0.3 |

*Bacterial cultures were grown as described previously.
**The ability of bacteria to enter into MDCK cells (passage 8 to 10) during one hour was measured as described previously. Assay values represent the average of two separate assays and were normalized such that the invasiveness of bacteria from the non-agitated cultures equals 100%. The actual percent of the inoculum from the non-agitated cultures that entered the MDCK cells was 1.6% and 1.7% for Expts. I and II, respectively.

Invasiveness of a S. typhimurium mutant defective in anaerobic regulation.

33 proteins of S. typhimurium that increase in synthesis in response to anaerobiosis have been detected by two-dimensional gel electrophoresis and subsequently identified (Spector, M. P., Aliabadi, Z., Gonzaler, T. & Foster, J. W. (1986) J. Bacteriol. 168: 420–424.). The oxrA locus of S. typhimurium is required for the regulation of 14 of these proteins (Strauch, K. L., Lenk, J. B., Gamble, B. L. & Miller, C. G. (1985) J. Bacteriol. 161: 673–680, Spector, M. P., Aliabadi, Z., Gonzaler, T. & Foster, J. W. (1986) J. Bacteriol. 168: 420–424.). The OxrA protein is homologous to the Fnr protein of Escherichia coli which functions as an oxygen-sensitive transcriptional activator during anaerobiosis (Strauch, K. L., Lenk, J. B., Gamble, B. L. & Miller, C. G. (1985) J. Bacteriol. 161: 673–680, Sprio, S. & Guest, J. R. (1988) Molec. Microbiol. 2, 701–707, Trageser, M. & Unden, G. (1989) Molec. Microbiol. 3: 593–599.). Since the expression of Salmonella invasiveness is induced in oxygen-limited growth conditions, the invasiveness of isogenic oxrA+/oxrA− S. typhimurium strains grown in aerobic and oxygen-limited conditions was examined. The oxrA+ and oxrA− strains were shown not to differ in their ability to enter MDCK cells. Both strains exhibited a 100-fold increase in invasiveness when grown in oxygen-limited vs. aerobic conditions. Thus, the oxrA locus does not regulate the expression of Salmonella invasiveness.

Adherence and entry of Salmonella choleraesuis to MDCK cells

It has been proposed that Salmonella initially bind to the mammalian cell surface and are subsequently internalized by a host-direct endocytic/phagocytic process (Finlay, B. B. & Falkow, S. (1988) Biochimie 70: 1089–1099, Moulder, J. W. (1985) Microbiol. Rev. 49: 298–337.). Thus, alteration of either the binding properties or the efficiency of the internalization process would affect bacterial invasiveness. S. choleraesuis grown in different cultures conditions were examined for changes in their ability to bind to, and subsequently enter MDCK cells. A similar assay for adherence and internalization has been used to examine the interaction between the Yersinia pseudotuberculosis invasion protein and its mammalian receptor (Isberg, R. R. (1989) Molec.

*Microbiol.* 3:1449–1453, Isberg, R. R., Voorhis, D. L. & Falkow, S. (1987) *Cell* 50:769–778.).

Although *S. choleraesuis* does not bind efficiently to MDCK cells in this assay, the data in Table 8 revealed that bacteria from oxygen-limited cultures were able to adhere to MDCK cells 20- to 100-fold better than bacteria from aerobic cultures. Bacteria from stationary phase also appeared to adhere to MDCK cells. Measurement of the number of adherent bacteria that were able to subsequently enter the MDCK cells demonstrated that a relatively high percentage of bacteria were internalized in all cases, except for the bacteria from stationary phase. Adherent stationary phase bacteria were internalized 100-fold less efficiently, a finding consistent with previous observations that such bacteria are not invasive.

TABLE 8

Adherence and subsequent internalization of *S. choleraesuis* into MDCK cells

| Expt. #* | Bacterial culture** | Bacterial adherence at 0° C.(%)*** | Internalization of adherent bacteria at 37° C.(%)§ |
|---|---|---|---|
| I | non-agitated, late log | 100 ± 15 | 59 ± 7 |
|  | agitated, late log | 26 ± 1 | 35 ± 2 |
|  | agitated, mid-log | 0.8 ± 0.5 | 54 ± 11 |
|  | stationary phase | 22 ± 2 | 0.3 ± 0.1 |
| II | non-agitated, late log | 100 ± 8 | 40 ± 5 |
|  | agitated, late log | 40 ± 0.5 | 16 ± 9 |
|  | agitated, mid-log | 6 ± 0.4 | 15 ± 6 |
|  | stationary phase | 83 ± 16 | 0.4 ± 0.1 |
| III | non-agitated, late log | 100 ± 16 | 7 ± 0.1 |
|  | agitated, late log | 83 ± 8 | 7 ± 2 |
|  | agitated, mid-log | 58 ± 7 | 9 ± 0.3 |
|  | stationary phase | 2 ± 1 | II |

*MDCK cells between passage 40 and 60 were used for Expt. I and II whereas those between passage 8 and 10 were used for Expt. III.
**Bacterial cultures were prepared as described above.
***Assay values represent the average of two separate assays and were normalized such that the adherence of bacteria from the non-agitated cultures equal 100%. The actual percent of the inoculum from the non-agitated cultures that were adherent was 1.6%, 1.2% and 0.12% for Expts. I, II and III, respectively.
§Values represent the average of two separate assays.
IIValues were too low to allow calculation.

Induction of S. choleraesuis invasiveness in the presence and absence of MDCK cells Previous experiments have shown that *S. choleraesuis* grown overnight in LB broth is not inherently able to enter MDCK cells. However, after further incubation with the mammalian cells in tissue culture medium, bacteria adherence and invasiveness was induced. It has been proposed that induction of invasiveness might occur in response to exposure to the epithelial cell surface (Finlay, B. B., Heffron, F. & Falkow, S. (1989) *Science* 243: 940–943.). The induction of invasiveness seen in the experiment in Table 8 may have been due to the presence of the MDCK cells, or to a change in bacterial growth state during the incubation period. Experiments to distinguish between these two possibilities were performed by comparing the invasiveness of *S. choleraesuis* incubated with MDCK cells vs. *S. choleraesuis* incubated identically in tissue culture media but in the absence of MDCK cells. The results obtained revealed that regardless of the presence of MCCK cells, bacterial invasiveness was induced 40-fold after four hours of incubation. Thus in this in vitro system, induction of Salmonella invasiveness can be accounted for by growth in tissue culture media alone.

Analysis of proteins synthesized by invasive Salmonella

In order to identify the major proteins expressed by invasive *Salmonella, S. choleraesuis* and *S. typhi* grown under different culture conditions were radiolabelled. Invasive bacteria from non-agitated cultures were compared with bacteria from agitated culture (which are at least 10-fold less invasive than the bacteria grown in the non-agitated). Proteins with approximate molecular weights of 65 Kd and 44 Kd were found to be preferentially produced by invasive Salmonella. By comparison to previously published protein patterns, it appears that both of these proteins have been identified as expressed by Salmonella adherent to MDCK cells (Finlay, B. B., Heffron, F. & Falkow, S. (1989) *Science* 243:940–943.).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid comprising at least 50 nucleotides of a *Yersinia inv* structural gene.

2. The nucleic acid of claim 1 wherein said inv gene is the *Yersinia enterocolitica* or *Yersinia pseudotuberculosis* structural gene.

3. A nucleic acid encoding a *Yersinia inv* structural gene or fragment thereof, said nucleic acid or fragment consisting essentially of at least 50 nucleotides and not more than 50 kilo nucleotides.

4. The nucleic acid of claim 3 wherein said inv structural gene in the *Yersinia enterocolitica* or *Yersinia pseudotuberculosis* inv gene.

5. An isolated nucleic acid comprising transcriptional and translational initiation and termination regions functional in a microorganism host operably linked to a region encoding the expression product of a *Yersinia inv* structural gene.

6. The nucleic acid of claim 5 wherein said inv gene is the *Yersinia enterocolitica* or *Yersinia pseudotuberoulosis* gene.

7. A nucleic acid comprising transcriptional and translational initiation and termination regions functional in a microorganism host operably linked to a region encoding the expression product of a *Yersinia inv* gene, wherein said initiation region is other than the wild type region of said *Yersinia inv* gene.

8. The nucleic acid of claim 7 wherein said inv gene is the *Yersinia enterocolitica* or *Yersinia pseudotuberculosis inv* gene.

9. An isolated nucleic acid comprising transcriptional and translational initiation and termination regions functional in a microorganism host operably linked to a region encoding a fragment of the expression product of a *Yersinia inv* gene, wherein said fragment is encoded by at least 50 nucleotides.

10. The nucleic acid of claim 9 wherein said inv gene is the *Yersinia enterocolitica* or *Yersinia pseudotuberculosis* inv gene.

11. A nucleic acid comprising transcriptional and translational initiation and termination regions functional in a microorganism host operably linked to a region encoding a fragment of the expression product of a *Yersinia inv* gene, wherein said fragment is encoded by at least 50 nucleotides and wherein said initiation region is other than the wild type region of said *Yersinia inv* gene.

12. The nucleic acid of claim 11 wherein said inv gene is the *Yersinia enterocolitica* or *Yersinia pseudotuberculosis* inv gene.

13. A nucleic acid comprising a *Yersinia inv* gene, wherein said nucleic acid is contained within a microorganism other than the microorganism from which said inv gene is derived.

14. The nucleic acid of claim 13 wherein said inv gene further comprises transcriptional and translational initiation and termination regions from said inv gene.

15. The nucleic acid of claim 11 wherein said inv gene is the *Yersinia enterocolitica* or *Yersinia pseudotuberculosis* inv gene.

* * * * *

UNITED STATES PATENT AND TRADEMARK OFFICE
CERTIFICATE OF CORRECTION

PATENT NO. : 5,338,842
DATED : August 16, 1994
INVENTOR(S) : Ralph R. Isberg et al.

It is certified that error appears in the above-indentified patent and that said Letters Patent is hereby corrected as shown below:

Column 2, line 53, please change "Joined" to --joined--.
Column 4, line 66, please change "Joining" to --joining--.
Column 5, line 48, please change "cryptococcus" to --Cryptococcus--.
Column 6, line 28, please change "all" to --*ail*--.
Column 7, line 52, please change "all" to --*ail*--.
Column 9, line 63, please change "c18570am23Pam80" to --cI8570am23Pam80--.
Column 9, line 67, please change "μlac5" to --λlac5--.
Column 10, line 2, please replace "-" with --.--.
Column 10, line 29, please change "Hu/nan" to --Human--.
Column 11, line 64, please delete ".".
Column 11, line 67, please delete "s,".
Column 13, line 41, please change "type 1 pill, PAP pill," to read --type 1 pili, PAP pili--.
Column 15, line 44, please change "Bacb" to --Bach--.
Column 16, line 66, please replace "-" with --.--.
Column 17, line 63, please change "all" to --*ail*--.

UNITED STATES PATENT AND TRADEMARK OFFICE
CERTIFICATE OF CORRECTION

PATENT NO. : 5,338,842

DATED : August 16, 1994

INVENTOR(S) : Ralph R. Isberg et al.

It is certified that error appears in the above-indentified patent and that said Letters Patent is hereby corrected as shown below:

Column 17, line 68, please change "All" to --*Ail*--.

Column 18, line 1, please change "All" to --*Ail*--.

Column 18, line 3, please change "all" to --*ail*--.

Column 20, line 20, please change "fatally" to --family--.

Column 20, line 63, please delete "I" after "probe".

Column 21, line 28, please change "in, and all" to read --inv and *ail*--.

Column 21, line 36, please change "21,365-377" to --21:365-377--.

Column 21, line 65, please change "phimuriuan" to --phimurium--.

Column 22, line 16, please change "227,680-685" to --227:680-685--.

Column 22, line 40, please change "pboA" to --PhoA--.

Column 22, line 43, please change "Junctions" to --junctions--.

Column 23, line 6, please change "Mount" to --amount--.

UNITED STATES PATENT AND TRADEMARK OFFICE
CERTIFICATE OF CORRECTION

PATENT NO. : 5,338,842
DATED : August 16, 1994
INVENTOR(S) : Ralph R. Isberg et al.

It is certified that error appears in the above-indentified patent and that said Letters Patent is hereby corrected as shown below:

Column 24, line 3, please change "Junctions" to --junctions--.

Column 24, line 17, please change "Yon" to --Von--.

Column 24, line 32, please change "pi" to --pI--.

Column 25, line 3, please change "All" to --*Ail*--.

Column 25, line 14, please change "lysogene" to --lysogens--.

Column 26, line 6, please change "antigene" and "pathogene" to --antigens-- and --pathogens--.

Column 26, lines 8 and 10, please change "pathogene" to --pathogens--.

Column 26, line 17, please change "404Tywere" to read --404Ty were--.

Column 26, line 19, please change "aaroA148" to --ΔaroA148--.

Column 26, line 52, please delete "." after "-2X10$^8$".

Column 26, line 67, please change "nun" to --mm--.

Column 27, line 4, please change "CFU ml" to read --CFU/ml--.

UNITED STATES PATENT AND TRADEMARK OFFICE
CERTIFICATE OF CORRECTION

PATENT NO. : 5,338,842
DATED : August 16, 1994
INVENTOR(S) : Ralph R. Isberg et al.

It is certified that error appears in the above-indentified patent and that said Letters Patent is hereby corrected as shown below:

Column 28, line 33, after "above", please insert --.--.

Column 29, line 54, please change "161, 673-680" to read --161:673-680--.

Column 29, line 60, please change "ar" to read --are--.

Column 30, line 46, please delete italics beginning with "Strains grown" through "exhibited a" at line 49.

Column 32, approximately line 45 (claim 4, line 2), please change "in" to --is--.

Column 32, approximately line 53 (claim 6, line 2), please change "*pseudotuberoulo*" to --*pseudotuberculo*--.

Signed and Sealed this

Twenty-eight Day of February, 1995

BRUCE LEHMAN

Attest:

Attesting Officer

Commissioner of Patents and Trademarks